(12) United States Patent
Simon et al.

(10) Patent No.: US 11,123,545 B2
(45) Date of Patent: Sep. 21, 2021

(54) DEVICES AND METHODS FOR NERVE STIMULATION

(71) Applicant: ElectroCore, Inc., Basking Ridge, NJ (US)

(72) Inventors: Bruce J. Simon, Mountain Lakes, NJ (US); Joseph P. Errico, Warren, NJ (US); John T. Raffle, Austin, TX (US)

(73) Assignee: ELECTROCORE, INC., Basking Ridge, NJ (US)

( * ) Notice: Subject to any disclaimer, the term of this patent is extended or adjusted under 35 U.S.C. 154(b) by 0 days.

(21) Appl. No.: 16/837,818

(22) Filed: Apr. 1, 2020

(65) Prior Publication Data

US 2020/0222695 A1 Jul. 16, 2020

Related U.S. Application Data

(60) Division of application No. 16/520,630, filed on Jul. 24, 2019, which is a division of application No.
(Continued)

(51) Int. Cl.
*A61N 1/36* (2006.01)
*A61N 1/04* (2006.01)
(Continued)

(52) U.S. Cl.
CPC ......... *A61N 1/0456* (2013.01); *A61N 1/0472* (2013.01); *A61N 1/36014* (2013.01);
(Continued)

(58) Field of Classification Search
CPC .... A61N 1/40; A61N 1/36014; A61N 1/0456; A61N 1/36171; A61N 1/36178; A61N 1/36157; A61N 1/36175; A61N 1/3787; A61N 1/08; A61N 1/36146; A61N 1/36196; A61N 1/36153; A61N 2005/0645;
(Continued)

(56) References Cited

U.S. PATENT DOCUMENTS 3,590,810 A 7/1971 Kopecky
4,196,737 A 4/1980 Bevilacqua
(Continued)

FOREIGN PATENT DOCUMENTS

EP 1967226 9/2008
EP 2777764 8/2015
(Continued)

OTHER PUBLICATIONS

Greicius et al., Functional connectivity in the resting brain: A network analysis of the default mode hypothesis, PNAS, Jan. 2003, vol. 100, No. 1, pp. 253-258.
(Continued)

*Primary Examiner* — Deborah L Malamud
(74) *Attorney, Agent, or Firm* — Farber LLC

(57) ABSTRACT

Methods and devices for stimulating a nerve in a patient include emitting an electrical signal near a target nerve within the patient. The electrical signal comprises bursts of about 2 to about 20 pulses and the pulses oscillate between a positive voltage and a negative voltage within each burst.

21 Claims, 8 Drawing Sheets

Related U.S. Application Data

15/149,406, filed on May 9, 2016, now Pat. No. 10,363,415, which is a division of application No. 14/337,930, filed on Jul. 22, 2014, now Pat. No. 9,333,347, which is a continuation of application No. 13/075,746, filed on Mar. 30, 2011, now Pat. No. 8,874,205, which is a continuation-in-part of application No. 12/964,050, filed on Dec. 9, 2010, now abandoned, which is a continuation-in-part of application No. 12/859,568, filed on Aug. 19, 2010, now Pat. No. 9,037,247.

(60) Provisional application No. 61/451,259, filed on Mar. 10, 2011, provisional application No. 61/415,469, filed on Nov. 19, 2010.

(51) Int. Cl.
*A61N 2/00* (2006.01)
*A61N 1/40* (2006.01)

(52) U.S. Cl.
CPC ......... *A61N 1/36034* (2017.08); *A61N 2/006* (2013.01); *A61N 1/36053* (2013.01); *A61N 1/40* (2013.01)

(58) Field of Classification Search
CPC .... A61N 1/00; A61N 1/0496; A61N 1/36189; A61N 1/3625; A61N 1/37223; A61H 2201/5005; A61B 5/04001; A61B 5/6898; A61B 5/4041; A61B 5/6822
See application file for complete search history.

(56) References Cited

U.S. PATENT DOCUMENTS

| | | | |
|---|---|---|---|
| 4,989,605 A | 2/1991 | Rossen | |
| 5,109,847 A | 5/1992 | Liss et al. | |
| 5,458,141 A | 10/1995 | Neil | |
| 5,487,759 A | 1/1996 | Bastyr et al. | |
| 5,782,874 A | 7/1998 | Loos | |
| 5,899,922 A | 5/1999 | Loos | |
| 5,983,131 A | 11/1999 | Weaver et al. | |
| 6,341,236 B1 | 1/2002 | Osorio et al. | |
| 6,463,327 B1 | 10/2002 | Lurie et al. | |
| 6,587,719 B1 | 7/2003 | Barrett et al. | |
| 6,610,713 B2 | 8/2003 | Tracey | |
| 6,631,297 B1 | 10/2003 | Mo | |
| 7,254,444 B2 * | 8/2007 | Moore | A61N 1/36021 607/46 |
| 7,734,340 B2 | 6/2010 | De Ridder | |
| 7,797,041 B2 | 9/2010 | Libbus et al. | |
| 2002/0099417 A1 | 7/2002 | Naritoku et al. | |
| 2002/0183237 A1 | 12/2002 | Puskas | |
| 2002/0183804 A1 | 12/2002 | Malaney et al. | |
| 2003/0212311 A1 | 11/2003 | Nova et al. | |
| 2004/0073271 A1 | 4/2004 | Harry et al. | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0113630 A1 | 5/2005 | Fox et al. | |
| 2005/0137644 A1 | 6/2005 | Boveja et al. | |
| 2005/0187590 A1 | 8/2005 | Boveja et al. | |
| 2005/0216062 A1 | 9/2005 | Herbst | |
| 2005/0267544 A1 | 12/2005 | Lee et al. | |
| 2006/0074284 A1 | 4/2006 | Juola et al. | |
| 2006/0074450 A1 | 4/2006 | Boveja et al. | |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1 | 2/2007 | Parnis et al. | |
| 2007/0038264 A1 | 2/2007 | Jaax et al. | |
| 2007/0106337 A1 | 5/2007 | Errico et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0156182 A1 | 7/2007 | Castel et al. | |
| 2007/0276449 A1 | 11/2007 | Gunter et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0077192 A1 | 3/2008 | Harry et al. | |
| 2008/0114199 A1 | 5/2008 | Riehl et al. | |
| 2008/0132964 A1 | 6/2008 | Cohen et al. | |
| 2008/0177190 A1 | 7/2008 | Libbus et al. | |
| 2008/0208266 A1 | 8/2008 | Lesser et al. | |
| 2008/0306325 A1 | 12/2008 | Burnett et al. | |
| 2009/0036945 A1 * | 2/2009 | Chancellor | A61N 1/36175 607/39 |
| 2009/0099622 A1 * | 4/2009 | Fowler | A61N 1/36082 607/45 |
| 2009/0112283 A1 | 4/2009 | Kriksunov et al. | |
| 2009/0132018 A1 | 5/2009 | DiUbaldi et al. | |
| 2009/0157149 A1 | 6/2009 | Wahlgren et al. | |
| 2009/0234417 A1 | 9/2009 | Pastena et al. | |
| 2009/0234419 A1 | 9/2009 | Maschino et al. | |
| 2009/0240297 A1 | 9/2009 | Shavit et al. | |
| 2009/0287035 A1 | 11/2009 | Dietrich et al. | |
| 2010/0030299 A1 | 2/2010 | Covalin | |
| 2010/0152794 A1 | 6/2010 | Radivojevic et al. | |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |
| 2013/0006322 A1 | 1/2013 | Tai | |
| 2013/0060304 A1 | 3/2013 | LaTendresse et al. | |
| 2013/0245486 A1 | 9/2013 | Simon et al. | |
| 2014/0005743 A1 | 1/2014 | Giuffrida et al. | |
| 2015/0165226 A1 | 6/2015 | Simon et al. | |
| 2015/0190637 A1 | 7/2015 | Simon et al. | |

FOREIGN PATENT DOCUMENTS

| | | |
|---|---|---|
| JP | 2009-125263 | 6/2009 |
| KR | 101242190 | 3/2013 |
| WO | WO1993/01862 | 2/1993 |
| WO | WO2005/007120 | 1/2005 |
| WO | WO2007/092062 | 8/2007 |
| WO | WO2008/042902 | 4/2008 |
| WO | WO2007/058780 | 5/2008 |
| WO | WO2009/021080 | 2/2009 |
| WO | WO2009/064641 | 5/2009 |
| WO | WO2009/135693 | 11/2009 |
| WO | WO2012/121750 | 9/2012 |
| WO | WO2013/066135 | 5/2013 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Aug. 25, 2015 in related Application No. PCT/US15/31847 filed May 20, 2015 (10 pages).

International Search Report and Written Opinion dated May 8, 2007 in related PCT Application No. PCT/US2006/042823 filed Nov. 2, 2006 (5 pages).

International Search Report and Written Opinion dated Sep. 17, 2007 in related PCT Application No. PCT/US2006/042828 filed Nov. 2, 2006 (5 pages).

(56) References Cited

OTHER PUBLICATIONS

International Search Report and Written Opinion dated Mar. 26, 2008 in related PCT Application No. PCT/US2006/042752 filed Nov. 1, 2006 (7 pages).
International Search Report and Written Opinion dated Dec. 22, 2011 in related PCT Application No. PCT/US2011/049844 filed Aug. 31, 2011 (9 pages).
KR101242190 dated Mar. 25, 2013, Espacenet computer generated English translation (11 pages).
International Search Report and Written Opinion dated Apr. 30, 2013 in related PCT Application No. PCT/US2013/023014 filed Jan. 24, 2013 (7 pages).
International Search Report and Written Opinion dated Dec. 11, 2013 in related PCT Application No. PCT/US2013/058079 filed Sep. 4, 2013 (8 pages).
International Search Report and Written Opinion dated Jan. 29, 2014 in related PCT Application No. PCT/US2013/068804 filed Nov. 6, 2013 (10 pages).
Europe Office Action dated Apr. 24, 2018 in related Application No. 15796247.3 filed May 20, 2015 (6 pages).
Europe Office Action dated Jul. 26, 2018 in related Application No. 11818591.7 filed Aug. 12, 2011 (8 pages).

\* cited by examiner

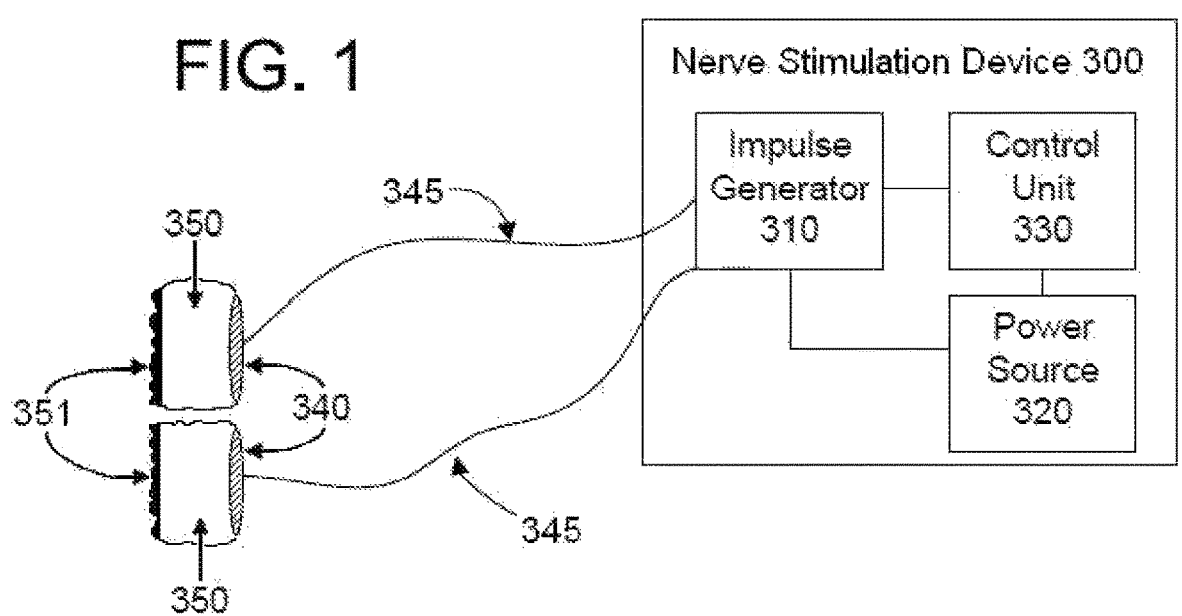

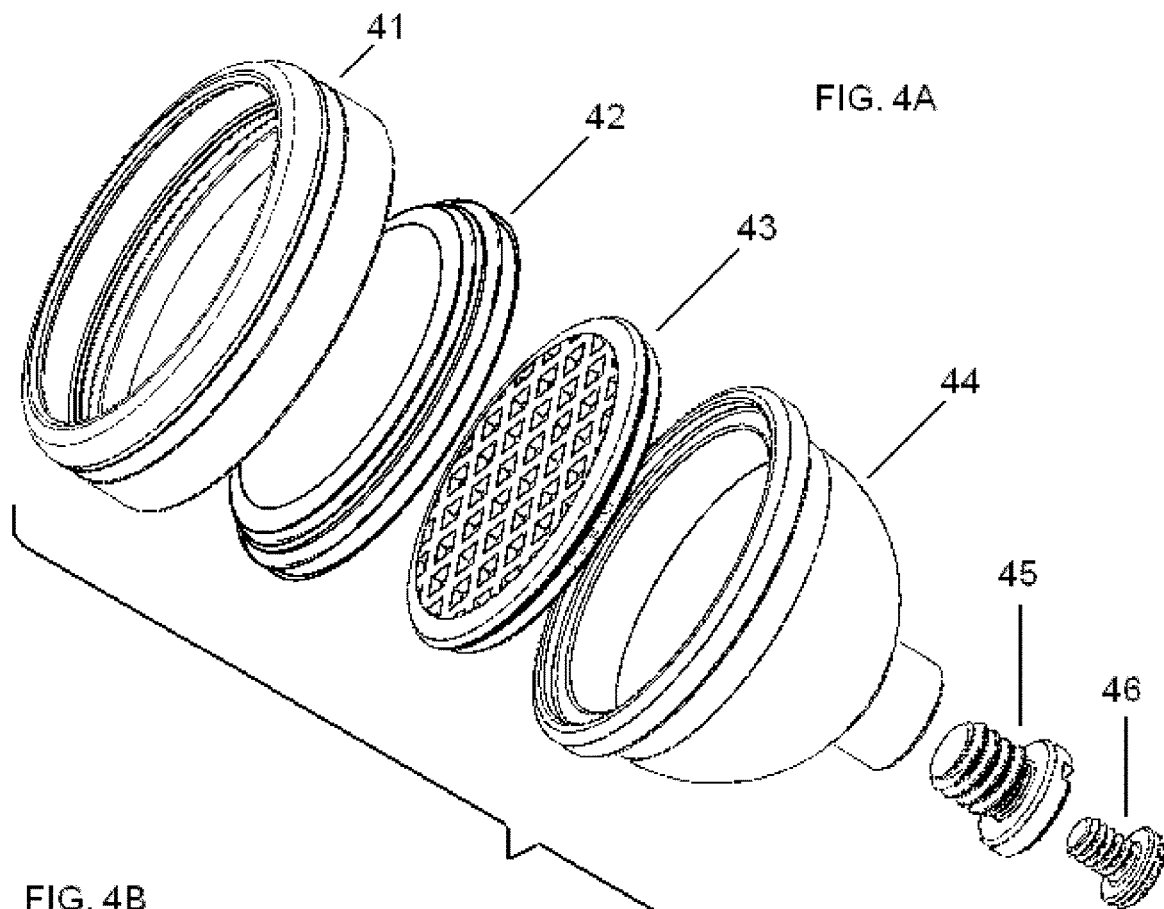
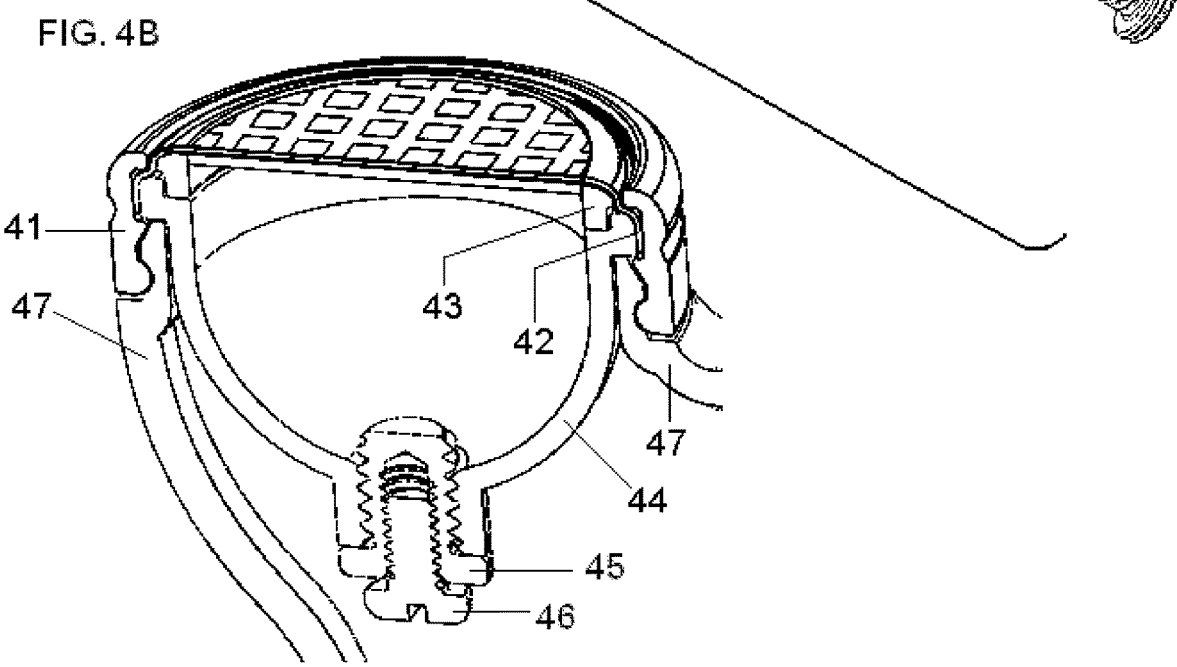

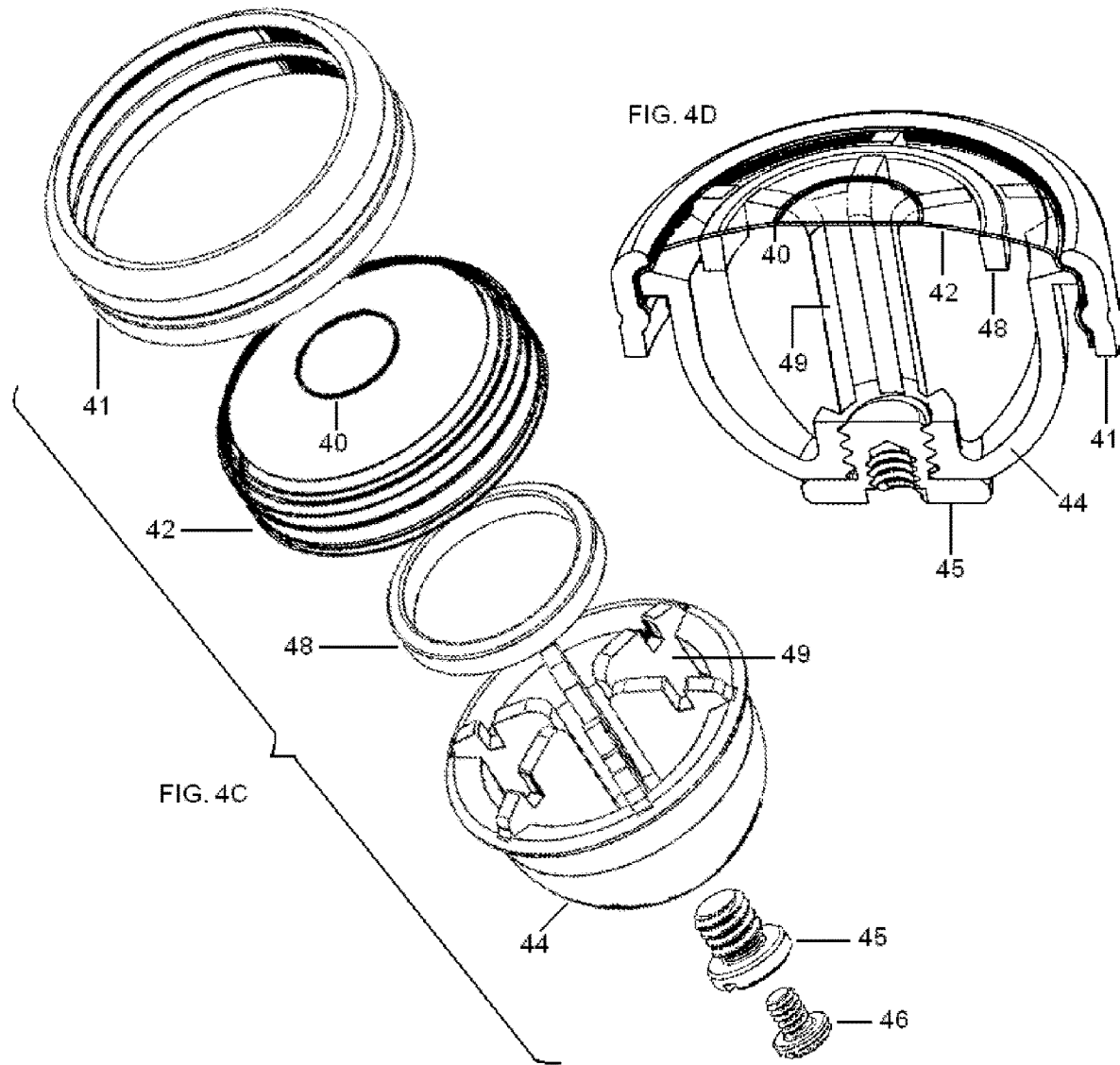

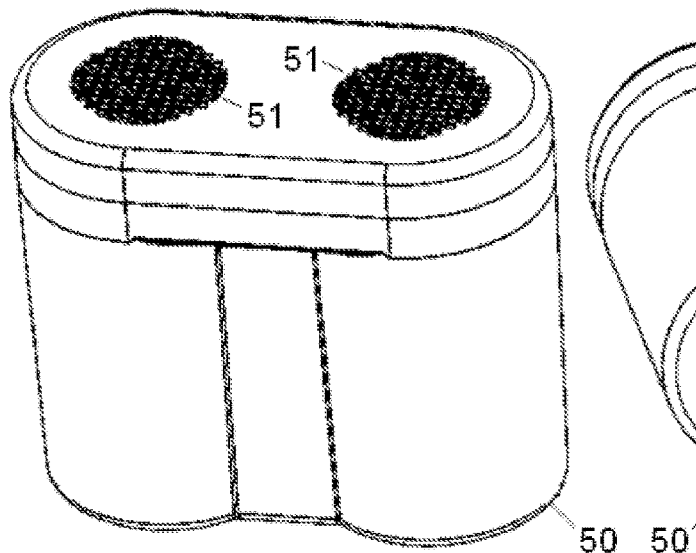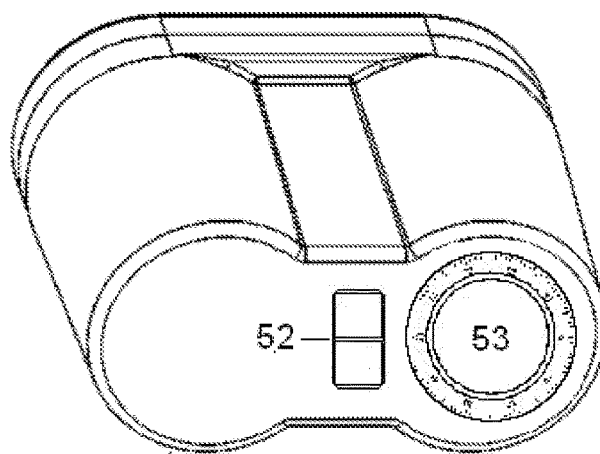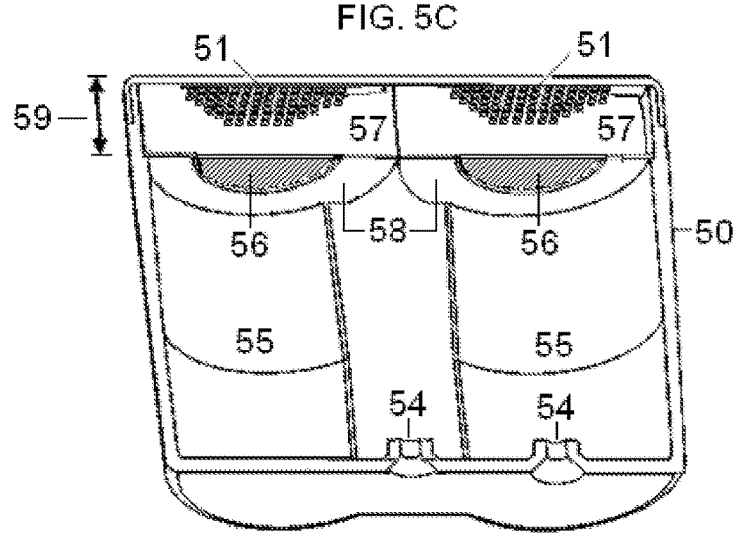

DEVICES AND METHODS FOR NERVE STIMULATION

CROSS REFERENCE TO RELATED APPLICATIONS

This application is a Divisional of U.S. Non-Provisional application Ser. No. 16/520,630, filed Jul. 24, 2019, which is a Divisional of U.S. Non-Provisional application Ser. No. 15/149,406 filed 9 May 2016 (now U.S. Pat. No. 10,363,415 issued Jul. 30, 2019); which is a Divisional of U.S. Non-Provisional application Ser. No. 14/337,930 filed 22 Jul. 2014 now U.S. Pat. No. 9,333,347 issued 10 May 2016; which is a Continuation of U.S. Non-Provisional application Ser. No. 13/075,746 filed 30 Mar. 2011 now U.S. Pat. No. 8,874,205 issued 28 Oct. 2015, which (i) claims the benefit of priority to U.S. Provisional Application Ser. No. 61/451,259 filed 10 Mar. 2011, and (ii) is a Continuation in Part of U.S. Non-Provisional application Ser. No. 12/964,050 filed 9 Dec. 2010, which (i) claims the benefit of priority to U.S. Provisional Application Ser. No. 61/415,469 filed 19 Nov. 2010, and (ii) is a Continuation in Part of U.S. Non-Provisional application Ser. No. 12/859,568 filed 19 Aug. 2010 now U.S. Pat. No. 9,037,247 issued 19 May 2015; each of which is fully incorporated by reference herein for all purposes.

BACKGROUND

The field of the present invention relates to the delivery of energy impulses (and/or fields) to bodily tissues for therapeutic purposes. It relates more specifically to the use of non-invasive devices and methods, particularly transcutaneous electrical nerve stimulation devices, as well as methods of treating patients using energy that is delivered by such devices. The disclosed methods and devices may be used to stimulate the vagus nerve of a patient to treat many conditions, such as: headaches such as migraine headaches, tension headaches, sinus headaches, cluster headaches and the like, allergic rhinitis, post-operative ileus, dysfunction associated with TNF-alpha in Alzheimer's disease, postoperative cognitive dysfunction, postoperative delirium, rheumatoid arthritis, asthmatic bronchoconstriction, urinary incontinence and/or overactive bladder, and sphincter of Oddi dysfunction, as well as neurodegenerative diseases more generally, including essential tremor, Alzheimer's disease and its precursor mild cognitive impairment (MCI), Parkinson's disease (including Parkinson's disease dementia) and multiple sclerosis.

Treatments for various infirmities sometime require the destruction of otherwise healthy tissue in order to produce a beneficial effect. Malfunctioning tissue is identified and then lesioned or otherwise compromised in order to produce a beneficial outcome, rather than attempting to repair the tissue to its normal functionality. A variety of techniques and mechanisms have been designed to produce focused lesions directly in target nerve tissue, but collateral damage is inevitable.

Other treatments for malfunctioning tissue can be medicinal in nature, but in many cases the patients become dependent upon artificially synthesized chemicals. In many cases, these medicinal approaches have side effects that are either unknown or quite significant. Unfortunately, the beneficial outcomes of surgery and medicines are often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue holds significant promise for the treatment of many ailments, because such stimulation is generally a wholly reversible and non-destructive treatment.

Nerve stimulation is thought to be accomplished directly or indirectly by depolarizing a nerve membrane, causing the discharge of an action potential; or by hyperpolarization of a nerve membrane, preventing the discharge of an action potential. Such stimulation may occur after electrical energy, or also other forms of energy, are transmitted to the vicinity of a nerve [F. RATTAY. The basic mechanism for the electrical stimulation of the nervous system. Neuroscience 89 (2, 1999):335-346; Thomas HEIMBURG and Andrew D. Jackson. On soliton propagation in biomembranes and nerves. PNAS 102 (28, 2005): 9790-9795]. Nerve stimulation may be measured directly as an increase, decrease, or modulation of the activity of nerve fibers, or it may be inferred from the physiological effects that follow the transmission of energy to the nerve fibers.

One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference).

Another application of electrical stimulation of nerves has been the treatment of radiating pain in the lower extremities by stimulating the sacral nerve roots at the bottom of the spinal cord (see U.S. Pat. No. 6,871,099 to WHITEHURST, et al., the disclosure of which is incorporated herein by reference).

Electrical stimulation of the brain with implanted electrodes has also been approved for use in the treatment of various conditions, including movement disorders such as essential tremor and Parkinson's disease. The principle underlying these approaches involves disruption and modulation of hyperactive neuronal circuit transmission at specific sites in the brain. Unlike potentially dangerous lesioning procedures in which aberrant portions of the brain are physically destroyed, electrical stimulation is achieved by implanting electrodes at these sites. The electrodes are used first to sense aberrant electrical signals and then to send electrical pulses to locally disrupt pathological neuronal transmission, driving it back into the normal range of activity. These electrical stimulation procedures, while invasive, are generally conducted with the patient conscious and a participant in the surgery.

However, brain stimulation, and deep brain stimulation in particular, is not without some drawbacks. The procedure requires penetrating the skull, and inserting an electrode into brain matter using a catheter-shaped lead, or the like. While monitoring the patient's condition (such as tremor activity, etc.), the position of the electrode is adjusted to achieve significant therapeutic potential. Next, adjustments are made to the electrical stimulus signals, such as frequency, intervalicity, voltage, current, etc., again to achieve therapeutic results. The electrode is then permanently implanted, and wires are directed from the electrode to the site of a surgically implanted pacemaker. The pacemaker provides the electrical stimulus signals to the electrode to maintain the therapeutic effect. While the therapeutic results of deep brain stimulation are promising, significant complications may arise from the implantation procedure, including stroke induced by damage to surrounding tissues and the neurovasculature.

Most of the above-mentioned applications of electrical stimulation involve the surgical implantation of electrodes within a patient. In contrast, for embodiments of the present invention, the disclosed devices and medical procedures stimulate nerves by transmitting energy to nerves and tissue non-invasively. They may offer the patient an alternative that does not involve surgery. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that invasive procedures do involve inserting a substance or device into or through the skin or into an internal body cavity beyond a body orifice. For example, transcutaneous electrical nerve stimulation (TENS) is non-invasive because it involves attaching electrodes to the surface of the skin (or using a form-fitting conductive garment) without breaking the skin. In contrast, percutaneous electrical stimulation of a nerve is minimally invasive because it involves the introduction of an electrode under the skin, via needle-puncture of the skin (see commonly assigned U.S. Patent Application 2010/0241188, entitled Percutaneous Electrical Treatment of Tissue to ERRICO et al, which is hereby incorporated by reference in its entirety).

Potential advantages of non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures generally present fewer problems with biocompatibility. In cases involving the attachment of electrodes, non-invasive methods have less of a tendency for breakage of leads, and the electrodes can be easily repositioned if necessary. Non-invasive methods are sometimes painless or only minimally painful and may be performed without the need for even local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace, and the cost of non-invasive procedures may be reduced relative to comparable invasive procedures.

Electrodes that are applied non-invasively to the surface of the body have a long history, including electrodes that were used to stimulate underlying nerves [L. A. GEDDES. Historical Evolution of Circuit Models for the Electrode-Electrolyte Interface. Annals of Biomedical Engineering 25 (1997):1-14]. However, electrical stimulation of nerves in general fell into disfavor in middle of the twentieth century, until the "gate theory of pain" was introduced by Melzack and Wall in 1965. This theory, along with advances in electronics, reawakened interest in the use of implanted electrodes to stimulate nerves, initially to control pain. Screening procedures were then developed to determine suitable candidates for electrode implantation, which involved first determining whether the patient responded when stimulated with electrodes applied to the surface of the body in the vicinity of the possible implant. It was subsequently found that the surface stimulation often controlled pain so well that there was no need to implant a stimulating electrode [Charles Burton and Donald D. Maurer. Pain Suppression by Transcutaneous Electronic Stimulation. IEEE Transactions on Biomedical Engineering BME-21 (2, 1974): 81-88]. Such non-invasive transcutaneous electrical nerve stimulation (TENS) was then developed for treating different types of pain, including pain in a joint or lower back, cancer pain, post-operative pain, post-traumatic pain, and pain associated with labor and delivery [Steven E. ABRAM. Transcutaneous Electrical Nerve Stimulation. pp 1-10 in: Joel B. Myklebust, ed. Neural stimulation (Volume 2). Boca Raton, Fla. CRC Press 1985; WALSH D M, Lowe A S, McCormack K. Willer J C, Baxter G D, Allen J M. Transcutaneous electrical nerve stimulation: effect on peripheral nerve conduction, mechanical pain threshold, and tactile threshold in humans. Arch Phys Med Rehabil 79(1998):1051-1058; J A CAMPBELL. A critical appraisal of the electrical output characteristics of ten transcutaneous nerve stimulators. Clin. phys. Physiol. Meas. 3 (2, 1982): 141-150; Patents U.S. Pat. No. 3,817,254, entitled Transcutaneous stimulator and stimulation method, to Maurer; U.S. Pat. No. 4,324,253, entitled Transcutaneous pain control and/or muscle stimulating apparatus, to Greene et al; U.S. Pat. No. 4,503,863, entitled Method and apparatus for transcutaneous electrical stimulation, to Katims; U.S. Pat. No. 5,052,391, entitled High frequency high intensity transcutaneous electrical nerve stimulator and method of treatment, to Silberstone et al; U.S. Pat. No. 6,351,674, entitled Method for inducing electroanesthesia using high frequency, high intensity transcutaneous electrical nerve stimulation, to Silverstone].

As TENS was being developed to treat pain, non-invasive electrical stimulation using surface electrodes was simultaneously developed for additional therapeutic or diagnostic purposes, which are known collectively as electrotherapy. Neuromuscular electrical stimulation (NMES) stimulates normally innervated muscle in an effort to augment strength and endurance of normal (e.g., athletic) or damaged (e.g., spastic) muscle. Functional electrical stimulation (FES) is used to activate nerves innervating muscle affected by paralysis resulting from spinal cord injury, head injury, stroke and other neurological disorders, or muscle affected by foot drop and gait disorders. FES is also used to stimulate muscle as an orthotic substitute, e.g., replace a brace or support in scoliosis management. Another application of surface electrical stimulation is chest-to-back stimulation of tissue, such as emergency defibrillation and cardiac pacing. Surface electrical stimulation has also been used to repair tissue, by increasing circulation through vasodilation, by controlling edema, by healing wounds, and by inducing bone growth. Surface electrical stimulation is also used for iontophoresis, in which electrical currents drive electrically charged drugs or other ions into the skin, usually to treat inflammation and pain, arthritis, wounds or scars. Stimulation with surface electrodes is also used to evoke a response for diagnostic purposes, for example in peripheral nerve stimulation (PNS) that evaluates the ability of motor and sensory nerves to conduct and produce reflexes. Surface electrical stimulation is also used in electroconvulsive therapy to treat psychiatric disorders; electroanesthesia, for example, to prevent pain from dental procedures; and electrotactile speech processing to convert sound into tactile sensation for the hearing impaired. All of the above-mentioned applications of surface electrode stimulation are intended not to damage the patient, but if higher currents are used with special electrodes, electrosurgery may be performed as a means to cut, coagulate, desiccate, or fulgurate tissue [Mark R. Prausnitz. The effects of electric current applied to skin: A review for transdermal drug delivery. Advanced Drug Delivery Reviews 18 (1996) 395-425].

Despite its attractiveness, non-invasive electrical stimulation of a nerve is not always possible or practical. This is primarily because the current state of the art may not be able to stimulate a deep nerve selectively or without producing excessive pain, since the stimulation may unintentionally stimulate nerves other than the nerve of interest, including nerves that cause pain. For this reason, forms of electrical stimulation other than TENS may be best suited for the treatment of particular types of pain [Paul F. WHITE, Shitong Li and Jen W. Chiu. Electroanalgesia: Its Role in Acute and Chronic Pain Management. Anesth Analg 92 (2001):505-13].

For some other electrotherapeutic applications, it has also been difficult to perform non-invasive stimulation of a nerve, in lieu of stimulating that nerve invasively. The therapies most relevant to the present invention involve electrical stimulation of the vagus nerve in the neck, in order to treat epilepsy, depression, and other medical conditions. For these therapies, the left vagus nerve is ordinarily stimulated at a location within the neck by first surgically implanting an electrode there, then connecting the electrode to an electrical stimulator [Patent numbers U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al and U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042-1060; GROVES D A, Brown V J. Vagal nerve stimulation: a review of its applications and potential mechanisms that mediate its clinical effects. Neurosci Biobehav Rev (2005) 29:493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3, 2008):E9, pp. 1-4].

When it is desired to avoid the surgical implantation of an electrode, vagal nerve stimulation (VNS) may be performed less invasively by positioning one or more electrodes in the esophagus, trachea, or jugular vein, but with one electrode positioned on the surface of the body [Patent No. U.S. Pat. No. 7,340,299, entitled Methods of indirectly stimulating the vagus nerve to achieve controlled asystole, to PUSKAS; and U.S. Pat. No. 7,869,884, entitled Non-surgical device and methods for trans-esophageal vagus nerve stimulation, to SCOTT et al]. Despite their advantage as being non-surgical, such methods nevertheless exhibit other disadvantages associated with invasive procedures.

In other patents, non-invasive VNS is disclosed, but at a location other than in the neck [e.g., U.S. Pat. No. 4,865,048, entitled Method and apparatus for drug free neurostimulation, to ECKERSON; U.S. Pat. No. 6,609,025 entitled Treatment of obesity by bilateral sub-diaphragmatic nerve stimulation to BARRETT et al; U.S. Pat. No. 5,458,625, entitled Transcutaneous nerve stimulation device and method for using same, to KENDALL; U.S. Pat. No. 7,386,347, entitled Electric stimulator for alpha-wave derivation, to Chung et al.; U.S. Pat. No. 7,797,042, entitled Device for applying a transcutaneous stimulus or for transcutaneous measuring of a parameter, to Dietrich et al.; patent application U.S.2010/0057154, entitled Device and Method for the Transdermal Stimulation of a Nerve of the Human Body, to Dietrich et al; U.S.2006/0122675, entitled Stimulator for auricular branch of vagus nerve, to Libbus et al; U.S.2008/0288016, entitled Systems and Methods for Stimulating Neural Targets, to Amurthur et al]. However, because such non-invasive VNS occurs at a location other than the neck, it is not directly comparable to invasive VNS in the neck, for which therapeutic results are well-documented. Among other patents and patent applications, non-invasive VNS is sometimes mentioned along with invasive VNS methods, but without addressing the problem of unintentional stimulation of nerves other than the vagus nerve, particularly nerves that cause pain [e.g., U.S.20080208266, entitled System and Method for Treating Nausea and Vomiting by Vagus Nerve Stimulation, to LESSER et al]. Other patents are vague as to how non-invasive electrical stimulation in the vicinity of the vagus nerve in the neck is to be accomplished [e.g., U.S. Pat. No. 7,499,747, entitled External baroreflex activation, to KIEVAL et al].

In view of the foregoing background, there is a long-felt but unsolved need to stimulate the vagus nerve electrically in the neck, totally non-invasively, selectively, and essentially without producing pain. As compared with what would have been experienced by a patient undergoing non-invasive stimulation with conventional TENS methods, the vagal nerve stimulator should produce relatively little pain for a given depth of stimulus penetration. Or conversely, for a given amount of pain or discomfort on the part of the patient (e.g., the threshold at which such discomfort or pain begins), an objective of some embodiments of the present invention is to achieve a greater depth of penetration of the stimulus under the skin. Furthermore, an objective of some embodiments of the present invention is to mitigate significant stimulation of other nerves and muscle that lie near the vagus nerve in the neck, but nevertheless to stimulate the vagus nerve to achieve therapeutic results.

SUMMARY OF THE DISCLOSURE

In one aspect of the invention, devices and methods are described to produce therapeutic effects in a patient by utilizing an energy source that transmits energy non-invasively to nervous tissue. In certain embodiments, the disclosed devices can transmit energy to, or in close proximity to, a vagus nerve in the neck of the patient, in order to temporarily stimulate, block and/or modulate electrophysiological signals in that nerve. The methods that are disclosed herein comprise stimulating the vagus nerve with particular stimulation waveform parameters, preferably using the nerve stimulator devices that are also described herein.

In one aspect of the invention, a novel stimulator device is used to modulate electrical activity of a vagus nerve or other nerves or tissue. The stimulator comprises a source of electrical power and one or more electrodes that are configured to stimulate a deep nerve relative to the nerve axis. The device also comprises continuous electrically conducting media within which the electrode(s) are in contact. The conducting media provides electrically communication between the electrode(s) and the patient's tissue such that the electrode(s) are not in direct contact with the tissue. The conducting medium preferably has a shape that conforms to the contour of a target body surface of a patient when the medium is applied to the target body surface For the present medical applications, the device is ordinarily applied to the patient's neck. In a preferred embodiment of the invention, the stimulator comprises two electrodes that lie side-by-side within separate stimulator heads, wherein the electrodes are separated by electrically insulating material. Each electrode and the patient's skin are in continuous contact with an electrically conducting medium that extends from the skin to the electrode. The conducting media for different electrodes are also separated by electrically insulating material.

The source of power supplies a pulse of electric charge to the electrode(s), such that the electrode(s) produce an electric current and/or an electric field within the patient. The stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at about 1,000 Hz. For example, the device may produce an electric field within the patient from about 10 to about 600 V/m and an electrical field gradient of greater than about 2 V/m/mm.

Current passing through an electrode may be from about 0 to about 40 mA, with voltage across the electrodes from about 0 to about 30 volts. The current is passed through the electrodes in bursts of pulses. There may be from about 2 to about 20 pulses per burst, preferably from about 4 to about 10 pulses and more preferably about five pulses. Each pulse within a burst has a duration from about 20 to about 1,000 microseconds, preferably from about 100 to about 400 microseconds and more preferably about 200 microseconds. A burst followed by a silent inter-burst interval repeats from about 1 to about 5000 bursts per second (bps), preferably from about 15 to about 50 bps. The preferred shape of each pulse is a full sinusoidal wave. The preferred stimulator shapes an elongated electric field of effect that can be oriented parallel to a long nerve, such as a vagus nerve in the patient's neck. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves that produce pain.

Teachings of the present invention demonstrate how the disclosed non-invasive stimulators may be positioned and used against body surfaces, particularly at a location on the patient's neck under which a vagus nerve is situated. Those teachings also describe the production of certain beneficial, therapeutic effects in a patient. However, it should be understood that application of the methods and devices is not limited to the examples that are given.

The novel systems, devices and methods for treating conditions using the disclosed stimulator or other non-invasive stimulation devices are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 1 is a schematic view of a nerve or tissue modulating device according to the present invention, which supplies controlled pulses of electrical current to electrodes that are continuously in contact with a volume filled with electrically conducting material.

FIG. 4A is an exploded view of one embodiment of the head of the dual-electrode stimulator that is shown in FIG. 3A.

FIG. 4B is a cross-sectional view of the head of FIG. 4A;

FIG. 4C is an exploded view of an alternative embodiment of a head for the dual-electrode stimulator shown in FIG. 3A.

FIG. 4D is a cross-sectional view of the head of FIG. 4C.

FIG. 5A is a perspective view of the top of an alternate embodiment of a dual-electrode stimulator according to the present invention.

FIG. 5B is a perspective view of the bottom of the dual-electrode stimulator of FIG. 5A.

FIG. 5C is a cross-sectional view of the dual-electrode stimulator of FIG. 5A.

DETAILED DESCRIPTION OF THE PREFERRED EMBODIMENTS

Figure 2A:
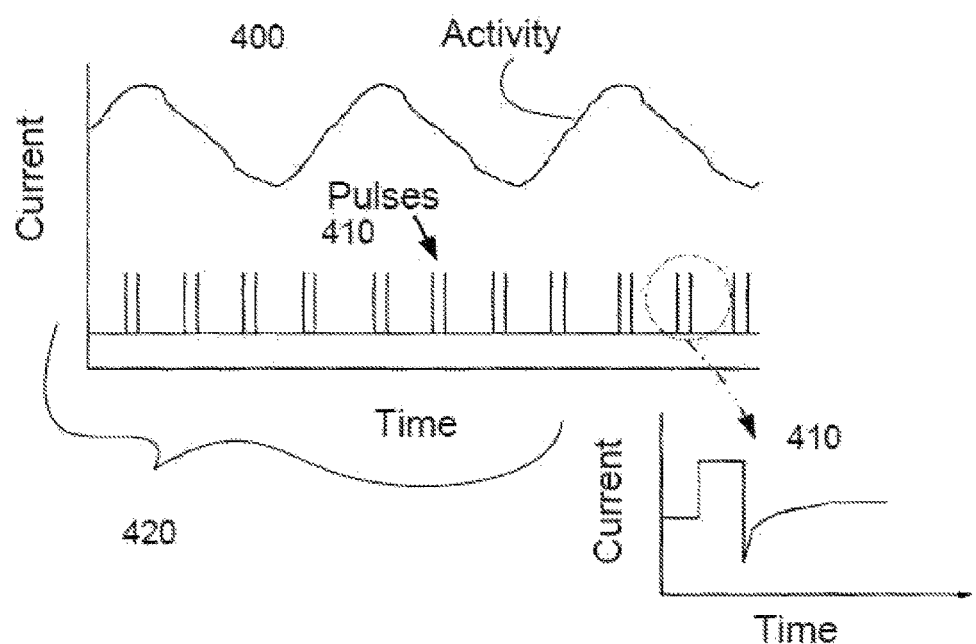
FIG. 2A illustrates an exemplary electrical voltage/current profile for a blocking and/or modulating impulses that are applied to a portion or portions of a nerve, in accordance with an embodiment of the present invention.

In the present invention, energy is transmitted non-invasively to a patient. The invention is particularly useful for producing applied electrical impulses that interact with the signals of one or more nerves to achieve a therapeutic result. In particular, the present disclosure describes devices and methods to stimulate a vagus nerve non-invasively at a location on the patient's neck.

There is a long-felt but unsolved need to stimulate the vagus nerve electrically in the neck, totally non-invasively, selectively, and essentially without producing pain. As described below, this is evidenced by the failure of others to solve the problem that is solved by the present invention, such that investigators abandoned the attempt to non-invasively stimulate electrically in the neck, in favor of stimulating the vagus nerve at other anatomical locations, or in favor of stimulating the vagus nerve non-electrically. Japanese patent application JP2009233024A with a filing date of Mar. 26, 2008, entitled Vagus Nerve Stimulation System, to Fukui YOSHIHITO, is concerned with stimulation of the vagus nerve on the surface of the neck to control heart rate, rather than epilepsy, depression, or other infirmities that vagal nerve stimulation (VNS) is ordinarily intended to treat. Nevertheless, the approach that is taken by Yoshihito illustrates the difficulties encountered with non-invasive electrical stimulation the vagus nerve. Yoshihito notes that because electrical stimulation on the surface of the neck may co-stimulate the phrenic nerve that is involved with the control of respiration, the patient hiccups and does not breathe normally, resulting in "a patient sense of incongruity and displeasure." Yoshihito's proposed solution to the problem is to modulate the timing and intensity of the electrical stimulation at the neck as a function of the respiratory phase, in such a way that the undesirable respiratory effects are minimized. Thus, Yoshihito's approach is to compensate for non-selective nerve stimulation, rather than find a way to stimulate the vagus nerve selectively. However, such compensatory modulation might also prevent the stimulation from achieving a beneficial effect in treating epilepsy, depression, and other infirmities that are ordinarily treated with VNS. Furthermore, Yoshihito does not address the problem of pain in the vicinity of the stimulation electrodes. Similar issues could conceivably arise in connection with possible co-stimulation of the carotid sinus nerve [Ingrid J. M. Scheffers, Abraham A. Kroon, Peter W. de Leeuw. Carotid Baroreflex Activation: Past, Present, and Future. Curr Hypertens Rep 12(2010):61-66]. Side effects due to co-activation of muscle that is controlled by the vagus nerve itself may also occur, which exemplify another type of non-selective stimulation [M Tosato, K Yoshida, E Toft and J J Struijk. Quasi-trapezoidal pulses to selectively block the activation of intrinsic laryngeal muscles during vagal nerve stimulation. J. Neural Eng. 4 (2007): 205-212].

One circumvention of the problem that the present invention solves is to non-invasively stimulate the vagus nerve at an anatomical location other than the neck, where the nerve lies closer to the skin. A preferred alternate location is in or around the ear (tragus, meatus and/or concha) although other locations have been proposed [Manuel L. KARELL. TENS in the Treatment of Heroin Dependency. The Western Journal of Medicine 125 (5, 1976):397-398; Enrique C. G. VENTUREYRA. Transcutaneous vagus nerve stimulation for partial onset seizure therapy. A new concept. Child's Nery Syst 16 (2000):101-102; T. KRAUS, K. Hosl, O. Kiess, A. Schanze, J. Kornhuber, C. Forster. BOLD fMRI deactivation of limbic and temporal brain structures and mood enhancing effect by transcutaneous vagus nerve stimulation. J Neural Transm 114 (2007): 1485-1493; POLAK T, Markulin F, Ehlis A C, Langer J B, Ringel T M, Fallgatter A J. Far field potentials from brain stem after transcutaneous vagus nerve stimulation: optimization of stimulation and recording parameters. J Neural Transm 116 (10, 2009):1237-1242; Patent U.S. Pat. No. 5,458,625, entitled Transcutaneous nerve stimulation device and method for using same, to KENDALL; U.S. Pat. No. 7,797,042, entitled Device for applying a transcutaneous stimulus or for transcutaneous measuring of a parameter, to Dietrich et al.; patent application U.S.2010/0057154, entitled Device and Method for the Transdermal Stimulation of a Nerve of the Human Body, to Dietrich et al; See also the non-invasive methods and devices that Applicant disclosed in commonly assigned U.S. patent application Ser. No. 12/859,568, entitled Non-invasive Treatment of Bronchial Constriction, to SIMON]. However, it is not certain that stimulation in this minor branch of the vagus nerve will have the same effect as stimulation of a main vagus nerve in the neck, where VNS electrodes are ordinarily implanted, and for which VNS therapeutic procedures produce well-documented results.

Another circumvention of the problem is to substitute electrical stimulation of the vagus nerve in the neck with some other form of stimulation. For example, mechanical stimulation of the vagus nerve on the neck has been proposed as an alternative to electrical stimulation [Jared M. HUSTON, Margot Gallowitsch-Puerta, Mahendar Ochani, Kanta Ochani, Renqi Yuan, Mauricio Rosas-Ballina, Mala Ashok, Richard S. Goldstein, Sangeeta Chavan, Valentin A. Pavlov, Christine N. Metz, Huan Yang, Christopher J. Czura, Haichao Wang, Kevin J. Tracey. Transcutaneous vagus nerve stimulation reduces serum high mobility group box 1 levels and improves survival in murine sepsis Crit Care Med 35 (12, 2007):2762-2768; Artur BAUHOFER and Alexander Torossian. Mechanical vagus nerve stimulation—A new adjunct in sepsis prophylaxis and treatment? Crit Care Med 35 (12, 2007):2868-2869; Hendrik SCHMIDT, Ursula Muller-Werdan, Karl Werdan. Assessment of vagal activity during transcutaneous vagus nerve stimulation in mice. Crit Care Med 36 (6, 2008):1990; see also the non-invasive methods and devices that Applicant disclosed in commonly assigned U.S. patent application Ser. No. 12/859,568, entitled Non-invasive Treatment of Bronchial Constriction, to SIMON]. However, such mechanical VNS has only been performed in animal models, and there is no evidence that such mechanical VNS would be functionally equivalent to electrical VNS.

Another circumvention of the problem is to use magnetic rather than purely electrical stimulation of the vagus nerve in the neck [Q. AZIZ et al. Magnetic Stimulation of Efferent Neural Pathways to the Human Oesophagus. Gut 33: S53-S70 (Poster Session F218) (1992); AZIZ, Q., J. C. Rothwell, J. Barlow, A. Hobson, S. Alani, J. Bancewicz, and D. G. Thompson. Esophageal myoelectric responses to magnetic stimulation of the human cortex and the extracranial vagus nerve. Am. J. Physiol. 267 (Gastrointest. Liver Physiol. 30): G827-G835, 1994; Shaheen HAMDY, Qasim Aziz, John C. Rothwell, Anthony Hobson, Josephine Barlow, and David G. Thompson. Cranial nerve modulation of human cortical swallowing motor pathways. Am. J. Physiol. 272 (Gastrointest. Liver Physiol. 35): G802-G808, 1997; Shaheen HAMDY, John C. Rothwell, Qasim Aziz, Krishna D. Singh, and David G. Thompson. Long-term reorganization of human motor cortex driven by short-term sensory stimulation. Nature Neuroscience 1 (issue 1, May 1998):64-68; A. SHAFIK. Functional magnetic stimulation of the vagus nerve enhances colonic transit time in healthy volunteers. Tech Coloproctol (1999) 3:123-12; see also the non-invasive methods and devices that Applicant disclosed in U.S. patent application Ser. No. 12/859,568 entitled Non-invasive Treatment of Bronchial Constriction, to SIMON, as well as co-pending U.S. patent application Ser. No. 12/964,050, entitled Magnetic Stimulation Devices and Methods of Therapy, to SIMON et al]. Magnetic stimulation might functionally approximate electrical stimulation. However, magnetic stimulation has the disadvantage that it ordinarily requires complex and expensive equipment, and the duration of stimulation may be limited by overheating of the magnetic stimulator. Furthermore, in some cases, magnetic stimulation in the neck might also inadvertently stimulate nerves other than the vagus nerve, such as the phrenic nerve [SIMILOWSKI, T., B. Fleury, S. Launois, H. P. Cathala, P. Bouche, and J. P. Derenne. Cervical magnetic stimulation: a new painless method for bilateral phrenic nerve stimulation in conscious humans. J. Appl. Physiol. 67(4): 1311-1318, 1989; Gerrard F. RAFFERTY, Anne Greenough, Terezia Manczur, Michael I. Polkey, M. Lou Harris, Nigel D. Heaton, Mohamed Rela, and John Moxham. Magnetic phrenic nerve stimulation to assess diaphragm function in children following liver transplantation. Pediatr Crit Care Med 2001, 2:122-126; W. D C. MAN, J. Moxham, and M. I. Polkey. Magnetic stimulation for the measurement of respiratory and skeletal muscle function. Eur Respir J 2004; 24: 846-860]. Furthermore, magnetic stimulation may also stimulate nerves that cause pain. Other stimulators that make use of magnetic fields might also be used, but they too are complex and expensive and may share other disadvantages with more conventional magnetic stimulators [Patent U.S. Pat. No. 7,699,768, entitled Device and method for non-invasive, localized neural stimulation utilizing hall effect phenomenon, to Kishawi et al].

Transcutaneous electrical stimulation (as well as magnetic stimulation) can be unpleasant or painful, in the experience of patients that undergo such procedures. The quality of sensation caused by stimulation depends strongly on current and frequency, such that currents barely greater than the perception threshold generally cause painless sensations described as tingle, itch, vibration, buzz, touch, pressure, or pinch, but higher currents can cause sharp or burning pain. As the depth of penetration of the stimulus under the skin is increased (e.g., to deeper nerves such as the vagus nerve), any pain will generally begin or increase. Strategies to reduce the pain include: use of anesthetics placed on or injected into the skin near the stimulation and placement of foam pads on the skin at the site of stimulation [Jeffrey J. BORCKARDT, Arthur R. Smith, Kelby Hutcheson, Kevin Johnson, Ziad Nahas, Berry Anderson, M. Bret Schneider, Scott T. Reeves, and Mark S. George. Reducing Pain and Unpleasantness During Repetitive Transcranial Magnetic Stimulation. Journal of ECT 2006; 22:259-264], use of nerve blockades [V. HAKKINEN, H. Eskola, A. Yli-Hankala, T. Nurmikko and S. Kolehmainen. Which structures are sensitive to painful transcranial stimulation? Electromyogr. clin. Neurophysiol. 1995, 35:377-383], the use of very short stimulation pulses [V. SUIHKO. Modelling the response of scalp sensory receptors to transcranial electrical stimulation. Med. Biol. Eng. Comput., 2002, 40, 395-401], decreasing current density by increasing electrode size [Kristof VERHOEVEN and J. Gert van Dijk. Decreasing pain in electrical nerve stimulation. Clinical Neurophysiology 117 (2006) 972-978], using a high impedance electrode [N. SHA, L. P. J. Kenney, B. W. Heller, A. T. Barker, D. Howard and W. Wang. The effect of the impedance of a thin hydrogel electrode on sensation during functional electrical stimulation. Medical Engineering & Physics 30 (2008): 739-746] and providing patients with the amount of information that suits their personalities [Anthony DELITTO, Michael J Strube, Arthur D Shulman, Scott D Minor. A Study of Discomfort with Electrical Stimulation. Phys. Ther. 1992; 72:410-424]. Patent U.S. Pat. No. 7,614,996, entitled Reducing discomfort caused by electrical stimulation, to RIEHL discloses the application of a secondary stimulus to counteract what would otherwise be an uncomfortable primary stimulus.

Additional considerations related to pain resulting from the stimulation are as follows. When stimulation is repeated over the course of multiple sessions, patients may adapt to the pain and exhibit progressively less discomfort. Patients may be heterogeneous with respect to their threshold for pain caused by stimulation, including heterogeneity related to gender and age. Electrical properties of an individual's skin vary from day to day and may be affected by cleaning, abrasion, and the application of various electrode gels and pastes. Skin properties may also be affected by the stimulation itself, as a function of the duration of stimulation, the recovery time between stimulation sessions, the transdermal voltage, the current density, and the power density. The application of multiple electrical pulses can result in different perception or pain thresholds and levels of sensation, depending on the spacing and rate at which pulses are applied. The separation distance between two electrodes determines whether sensations from the electrodes are separate, overlap, or merge. The limit for tolerable sensation is sometimes said to correspond to a current density of 0.5 $mA/cm^2$, but in reality the functional relationship between pain and current density is very complicated. Maximum local current density may be more important in producing pain than average current density, and local current density generally varies under an electrode, e.g., with greater current densities along edges of the electrode or at "hot spots." Furthermore, pain thresholds can have a thermal and/or electrochemical component, as well as a current density component. Pulse frequency plays a significant role in the perception of pain, with muscle contraction being involved at some frequencies and not others, and with the spatial extent of the pain sensation also being a function of frequency. The sensation is also a function of the waveform (square-wave, sinusoidal, trapezoidal, etc.), especially if pulses are less than a millisecond in duration [Mark R. PRAUSNITZ. The effects of electric current applied to skin: A review for transdermal drug delivery. Advanced Drug Delivery Reviews 18 (1996): 395-425].

Considering that there are so many variables that may influence the likelihood of pain during non-invasive electrical stimulation (detailed stimulus waveform, frequency, current density, electrode type and geometry, skin preparation, etc.), considering that these same variables can be simultaneously selected in order to independently produce a desired therapeutic outcome by vagal nerve stimulation, and considering that one also wishes to selectively stimulate the vagus nerve (e.g., avoid stimulating the phrenic nerve), it is understandable that prior to the present disclosure, no one has described devices and methods for stimulating the vagus nerve electrically in the neck, totally non-invasively, selectively, and without causing substantial pain.

Applicant discovered the disclosed devices and methods in the course of experimentation with a magnetic stimulation device that was disclosed in Applicant's commonly assigned U.S. patent application Ser. No. 12/964,050, entitled Magnetic Stimulation Devices and Methods of Therapy, to SIMON et al. Thus, combined elements in the invention do not merely perform the function that the elements perform separately (viz., perform therapeutic VNS, minimize stimulation pain, or stimulate the vagus nerve selectively), and one of ordinary skill in the art would not have combined the claimed elements by known methods because the archetypal magnetic stimulator was known only to Applicant. That stimulator used a magnetic coil, embedded in a safe and practical conducting medium that was in direct contact with arbitrarily-oriented patient skin, which had not been described in its closest art [Rafael CARBUNARU and Dominique M. Durand. Toroidal coil models for transcutaneous magnetic stimulation of nerves. IEEE Transactions on Biomedical Engineering 48 (4, 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999. (UMI Microform Number: 9940153, UMI Company, Ann Arbor Mich.)]. Such a design, which is adapted herein for use with surface electrodes, makes it possible to shape the electric field that is used to selectively stimulate a deep nerve such as a vagus nerve in the neck. Furthermore, the design produces significantly less pain or discomfort (if any) to a patient than stimulator devices that are currently known in the art. Conversely, for a given amount of pain or discomfort on the part of the patient (e.g., the threshold at which such discomfort or pain begins), the design achieves a greater depth of penetration of the stimulus under the skin.

FIG. 1 is a schematic diagram of a nerve stimulating/modulating device 300 for delivering impulses of energy to nerves for the treatment of medical conditions. As shown, device 300 may include an impulse generator 310; a power source 320 coupled to the impulse generator 310; a control unit 330 in communication with the impulse generator 310 and coupled to the power source 320; and electrodes 340 coupled via wires 345 to impulse generator 310.

Although a pair of electrodes 340 is shown in FIG. 1, in practice the electrode(s) may comprises a single electrode with a large surface area, or a plurality of distinct electrode elements, each of which is connected in series or in parallel to the impulse generator 310. Thus, the electrodes 340 that are shown in FIG. 1 represent all electrodes of the device collectively.

The item labeled in FIG. 1 as 350 is a volume, contiguous with an electrode 340, that is filled with electrically conducting medium. As shown in the preferred embodiment, the medium is also deformable such that it is form-fitting when applied to the surface of the body. Thus, the sinuousness or curvature shown at the outer surface of the electrically conducting medium 350 corresponds also to sinuousness or curvature on the surface of the body, against which the conducting medium 350 is applied, so as to make the medium and body surface contiguous. As described below in connection with a preferred embodiment, the volume 350 is electrically connected to the patient at a target skin surface in order to shape the current density passed through an electrode 340 that is needed to accomplish stimulation of the patient's nerve or tissue. As also described below in connection with exemplary embodiments of the invention, the conducting medium in which the electrode 340 is embedded need not completely surround an electrode.

The control unit 330 controls the impulse generator 310 to generate a signal for each of the device's electrodes. The signals are selected to be suitable for amelioration of a particular medical condition, when the signals are applied non-invasively to a target nerve or tissue via the electrodes 340. It is noted that nerve stimulating/modulating device 300 may be referred to by its function as a pulse generator. Patent application publications U.S.2005/0075701 and U.S.2005/0075702, both to SHAFER, both of which are incorporated herein by reference, relating to stimulation of neurons of the sympathetic nervous system to attenuate an immune response, contain descriptions of pulse generators that may be applicable to the present invention. By way of example, a pulse generator 300 is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard and computer mouse as well as any externally supplied physiological signals, analog-to-digital converters for digitizing externally supplied analog signals, communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurło, Przemysław Płonecki, Jacek Starzyński, Stanisław Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

FIG. 2A illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the electrodes 340 that deliver the stimulating, blocking and/or modulating impulse 410 to the nerve. Nerve stimulating/modulating device 300 may be externally powered and/or recharged may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes, the device disclosed in patent publication No. U.S.2005/0216062 (the entire disclosure of which is incorporated herein by reference) may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type the user wishes, who can then observe the effect of this signal on a substance being treated.

The stimulating, blocking and/or modulating impulse signal 410 preferably has a frequency, an amplitude, a duty cycle, a pulse width, a pulse shape, etc. selected to influence the therapeutic result, namely, stimulating, blocking and/or modulating some or all of the transmission of the selected nerve. For example, the frequency may be about 1 Hz or greater, such as between about 15 Hz to 50 Hz, more preferably around 25 Hz. The modulation signal may have a pulse width selected to influence the therapeutic result, such as about 20 microseconds or greater, such as about 20 microseconds to about 1,000 microseconds. For example, the electric field induced by the device within tissue in the vicinity of a nerve is 10 to 600 V/m, preferably around 300 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1,000 Hz.

An objective of some embodiments of the disclosed stimulator is to provide both nerve fiber selectivity and spatial selectivity. Spatial selectivity may be achieved in part through the design of the electrode configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385].

To date, the selection of stimulation waveform parameters for vagal nerve stimulation (VNS) has been highly empirical, in which the parameters are varied about some initially successful set of parameters, in an effort to find an improved set of parameters for each patient. A more efficient approach to selecting stimulation parameters might be to select a stimulation waveform that mimics electrical activity in the regions of the brain that one is attempting stimulate indirectly, in an effort to entrain the naturally occurring electrical waveform, as suggested in patent number U.S. Pat. No. 6,234,953, entitled Electrotherapy device using low frequency magnetic pulses, to THOMAS et al. and application number U.S.20090299435, entitled Systems and methods for enhancing or affecting neural stimulation efficiency and/or efficacy, to GLINER et al. One may also vary stimulation parameters iteratively, in search of an optimal setting [Patent U.S. Pat. No. 7,869,885, entitled Threshold optimization for tissue stimulation therapy, to Begnaud, et al]. However, some VNS stimulation waveforms, such as those described herein, are discovered by trial and error, and then deliberately improved upon.

Invasive vagal nerve stimulation typically uses square wave pulse signals. In some embodiments, the typical waveform parameter values for VNS therapy for epilepsy and depression are: a current between 1 and 2 mA, a frequency of between 20 and 30 Hz, a pulse width of 250-500 microseconds, and a duty cycle of 10% (signal ON time of 30 s, and a signal OFF time to 5 min). Output current is gradually increased from 0.25 mA to the maximum tolerable level (maximum, 3.5 mA), with typical therapeutic settings ranging from 1.0 to 1.5 mA. Greater output current is associated with increased side effects, including voice alteration, cough, a feeling of throat tightening, and dyspnea. Frequency is typically 20 Hz in depression and 30 Hz in epilepsy. The therapy is adjusted in a gradual, systematic fashion to individualize therapy for each patient. To treat migraine headaches, typical VNS parameters are a current of 0.25 to 1 mA, a frequency of 30 Hz, a pulse width of 500 microseconds, and an 'ON' time of 30 s every 5 min. To treat migraine plus epilepsy, typical parameters are 1.75 mA, a frequency of 20 Hz, a pulse width of 250 microseconds, and 'ON' time of 7 s followed by an 'OFF' time of 12 s. To treat mild to moderate Alzheimer's disease, typical VNS waveform parameters are: a current of 0.25 to 0.5 mA, a frequency of 20 Hz, a pulse width of 500 microseconds, and an 'ON' time of 30 s every 5 min. [ANDREWS, A. J., 2003. Neuromodulation. I. Techniques-deep brain stimulation, vagus nerve stimulation, and transcranial magnetic stimulation. Ann. N.Y. Acad. Sci. 993, 1-13; LABINER, D. M., Ahern, G. L., 2007. Vagus nerve stimulation therapy in depression and epilepsy: therapeutic parameter settings. Acta. Neurol. Scand. 115, 23-33; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009)

1042-1060]. Applicant found that these square waveforms are not ideal for non-invasive VNS stimulation as they produce excessive pain.

Prepulses and similar waveform modifications have been suggested as means to improve selectivity of vagus and other nerve stimulation waveforms, but Applicant did not find them ideal [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51 (5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figure 2B:
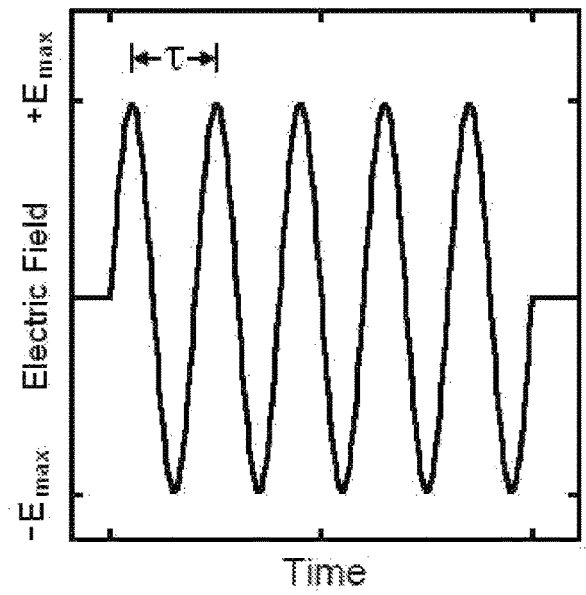
FIG. 2B illustrates a single burst of pulses for an electrical impulse according to the present invention.
Figure 2C:
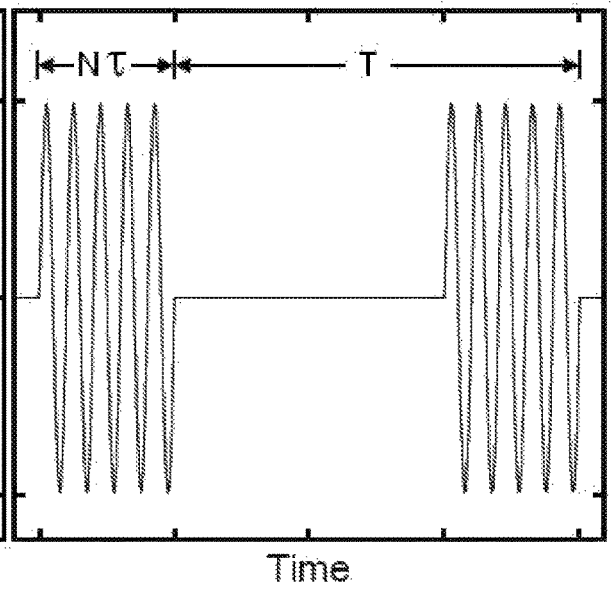
FIG. 2C illustrates an ON/OFF pattern for a pair of bursts of pulses according to the present invention.

Applicant also found that stimulation waveforms consisting of bursts of square pulses are not ideal for non-invasive VNS stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; Patent U.S. Pat. No. 7,734,340, entitled Stimulation design for neuromodulation, to De Ridder]. However, bursts of sinusoidal pulses are a preferred stimulation waveform, as shown in FIGS. 2B and 2C. As seen there, individual sinusoidal pulses have a interval of $\tau$, and a burst consists of N such pulses. This is followed by a interval with no signal (the inter-burst interval). The pattern of a burst plus followed by silent inter-burst interval repeats itself with a interval of T. For example, the sinusoidal interval $\tau$ may be between about 50 us to about 1 ms, preferably between about 100 us to 400 us, and more preferably about 200 microseconds; the number of pulses per burst (N) may be between about 2 to 20 pulses, preferably about 4 to 10 pulses and more preferably 5 pulses; and the whole pattern of burst followed by silent inter-burst interval may have a interval (T) of about 1 to 100 Hz, preferably about 10 to 35 Hz and more preferably about 25 Hz or 40000 microseconds (a much smaller value of T is shown in FIG. 2C to make the bursts discernable). Applicant is unaware of such a waveform having been used with vagal nerve stimulation, but a similar waveform has been used to stimulate muscle as a means of increasing muscle strength in elite athletes. However, for the muscle strengthening application, the currents used (200 mA) may be very painful and two orders of magnitude larger than what is disclosed herein for VNS. Furthermore, the signal used for muscle strengthening may be other than sinusoidal (e.g., triangular), and the parameters $\tau$, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10 (1989):187-191; Alex R WARD, Nataliya Shkuratova. Russian Electrical Stimulation: The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008):1167-1176; Alex R WARD. Electrical Stimulation Using Kilohertz-Frequency Alternating Current. Physical Therapy 89 (2, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181]. By way of example, the electric field shown in FIGS. 2B and 2C may have an Emax value of 17 V/m, which is sufficient to stimulate the vagus nerve but is significantly lower than the threshold needed to stimulate surrounding muscle.

In order to compare the stimulator that is disclosed herein with existing electrodes and stimulators used for non-invasive electrical stimulation, it is useful to first summarize the relevant physics of electric fields and currents that are produced by the electrodes. According to Maxwell's equation (Ampere's law with Maxwell correction): $\nabla \times B = J + \epsilon (\partial E / \partial t)$, where B is the magnetic field, J is the electrical current density, E is the electric field, $\epsilon$ is the permittivity, and t is time [Richard P. FEYNMAN, Robert B. Leighton, and Matthew Sands. The Feynman Lectures on Physics. Volume II. Addison-Wesley Publ. Co. (Reading Mass., 1964), page 15-15].

According to Faraday's law, $\nabla \times E = -\partial B / \partial t$. However, for present purposes, changes in the magnetic field B may be ignored, so $\nabla \times E = 0$, and E may therefore be obtained from the gradient of a scalar potential $\phi$: $E = -\nabla \phi$. In general, the scalar potential $\phi$ and the electric field E are functions of position (r) and time (t).

The electrical current density J is also a function of position (r) and time (t), and it is determined by the electric field and conductivity as follows, where the conductivity $\sigma$ is generally a tensor and a function of position (r): $J = \sigma E = -\sigma \nabla \phi$ Because $\nabla \nabla \times B = 0$, Ampere's law with Maxwell's correction may be written as: $\nabla \cdot J + \nabla \cdot \epsilon (\partial E / \partial t) = 0$. If the current flows in material that is essentially unpolarizable (i.e., is presumed not to be a dielectric so that $\epsilon = 0$), substitution of the expression for J into the above expression for Ampere's law gives $-\nabla \cdot (\sigma \nabla \phi) = 0$, which is a form of Laplace's equation. If the conductivity of material in the device (or patient) is itself a function of the electric field or potential, then the equation becomes non-linear, which could exhibit multiple solutions, frequency multiplication, and other such non-linear behavior. The equation has been solved analytically for special electrode configurations, but for more general electrode configurations, it can be solved numerically [Petrus J. CILLIERS. Analysis of the current density distribution due to surface electrode stimulation of the human body. Ph.D. Dissertation, Ohio State University, 1988. (UMI Microform Number: 8820270, UMI Company, Ann Arbor Mich.); Martin REICHEL, Teresa Breyer, Winfried Mayr, and Frank Rattay. Simulation of the Three-Dimensional Electrical Field in the Course of Functional Electrical Stimulation. Artificial Organs 26(3, 2002):252-255; Cameron C. McINTYRE and Warren M. Grill. Finite Element Analysis of the Current-Density and Electric Field Generated by Metal Microelectrodes. Annals of Biomedical Engineering 29 (2001): 227-235; A. PATRICIU, T. P. DeMonte, M. L. G. Joy, J. J. Struijk. Investigation of current densities produced by surface electrodes using finite element modeling and current density imaging. Proceedings of the 23rd Annual EM BS International Conference, Oct. 25-28, 2001, Istanbul, Turkey: 2403-2406; Yong H U, X B Xie, L Y Pang, X H Li K D K Luk. Current Density Distribution Under Surface Electrode on Posterior Tibial Nerve Electrical Stimulation. Proceedings of the 2005 IEEE Engineering in Medicine and Biology 27th Annual Conference Shanghai, China, Sep. 1-4, 2005: 3650-3652]. The equation has also been solved numerically in order to compare different electrode shapes and numbers [Abhishek DATTA, Maged Elwassif, Fortunato Battaglia and Marom Bikson. Transcranial current stimulation focality using disc and ring electrode configurations: FEM analysis. J. Neural Eng. 5 (2008) 163-174; Jay T. RUBENSTEIN, Francis A. Spelman, Mani Soma and Michael F. Suesserman. Current Density Profiles of Surface Mounted and Recessed Electrodes for Neural Prostheses. IEEE Transactions on Biomedical Engineering BME-34 (11, 1987): 864-875; David A. KSIENSKI. A Minimum Profile Uniform Current Density Electrode. IEEE Transactions on Biomedical Engineering 39 (7, 1992): 682-692; Andreas KUHN, Thierry Keller, Silvestro Micera, Manfred Morari. Array electrode design for transcutaneous electrical stimulation: A simulation study. Medical Engineering & Physics 31 (2009) 945-951]. The calculated electrical fields may be confirmed using measurements using a phantom [A. M. SAGI_DOLEV, D. Prutchi and R. H. Nathan. Three-dimensional current density distribution under surface stimulation electrodes. Med. and Biol. Eng. and Comput. 33(1995): 403-408].

If capacitive effects cannot be ignored, an additional term involving the time-derivative of the gradient of the potential appears in the more general expression, as obtained by substituting the expressions for J and E into the divergence of Ampere's law with Maxwell's correction:

$$-\nabla \cdot (\sigma \nabla \phi) - \nabla \cdot (\epsilon \nabla \phi (\partial \phi / \partial t)) = 0$$

The permittivity $\epsilon$ is a function of position (r) and is generally a tensor. It may result from properties of the body and may also be a property of the electrode design [L. A. GEDDES, M. Hinds and K. S. Foster. Stimulation with capacitor electrodes. Med. and Biol. Eng. and Comput. 25 (1987):359-360]. As a consequence of such a term, the waveform of the electrical potential at points within the body will generally be altered relative to the waveform of the voltage signal(s) applied to the electrode(s). Furthermore, if the permittivity of a material in the device itself (or patient) is a function of the electric field or potential, then the equation becomes non-linear, which could exhibit multiple solutions, frequency multiplication, and other such non-linear behavior. This time-dependent equation has been solved numerically [KUHN A, Keller T. A 3D transient model for transcutaneous functional electrical stimulation. Proc. 10th Annual Conference of the International FES Society July 2005—Montreal, Canada: pp. 1-3; Andreas KUHN, Thierry Keller, Marc Lawrence, Manfred Morari. A model for transcutaneous current stimulation: simulations and experiments. Med Biol Eng Comput 47 (2009):279-289; N. FILIPOVIC, M. Nedeljkovic, A. Peulic. Finite Element Modeling of a Transient Functional Electrical Stimulation. Journal of the Serbian Society for Computational Mechanics 1 (1, 2007):154-163; Todd A. KUIKEN, Nikolay S. Stoykov, Milica Popovic, Madeleine Lowery and Allen Taflove. Finite Element Modeling of Electromagnetic Signal Propagation in a Phantom Arm. IEEE Transactions on Neural Systems and Rehabilitation Engineering 9 (4, 2001): 346-354].

In any case, Dirichlet (D) boundary conditions define voltage sources, and Neumann (N) boundary conditions describe the behavior of the electric field at the crossover boundary from skin to air, as follows:

$$N: \partial \phi / \partial n = \sigma(r) \text{ and } D: \phi = V(t)$$

where n denotes the outward pointing normal vector, i.e., the vector orthogonal to the boundary curve; and V(t) denotes the voltage applied to an electrode. Thus, no conduction current can flow across an air/conductor interface, so according to the interfacial boundary conditions, the component of any current normal to the an air/conductor interface should be zero. In constructing the above differential equation for $\phi$ as a function of time, the divergence of J is taken, which satisfies the continuity equation: $\nabla \cdot J = -\partial \rho / \partial t$, where $\rho$ is the charge density. Conservation of charge requires that sides of this equation equal zero everywhere except at the surface of the electrode where charge is impressed upon the system (injected or received).

It is an objective of some embodiments of the present invention to shape an elongated electric field of effect that can be oriented parallel to a long nerve such as the vagus nerve in the neck. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which current flow is restricted. Shaping of the electric field refers both to the circumscribing of regions within which there is a significant electric field and to configuring the directions of the electric field within those regions. Our invention does so by configuring elements that are present within the equations that were summarized above, comprising (but not limited to) the following exemplary configurations that may be used alone or in combination.

First, different contours or shapes of the electrodes affect $\nabla \cdot J$. For example, charge is impressed upon the system (injected or received) differently if an electrode is curved versus flat, or if there are more than two electrodes in the system.

Second, values of the voltage V(t) in the above boundary condition is manipulated to shape the electric field. For example, if the device contains two pairs of electrodes that are perpendicular or at a variable angle with respect to one another, the waveform of the voltage across one pair of electrodes may be different than the waveform of the voltage across the second pair, so that the superimposed electric fields that they produce may exhibit beat frequencies, as has been attempted with electrode-based stimulators [Patent U.S. Pat. No. 5,512,057, entitled Interferential stimulator for applying localized stimulation, to REISS et al.], and acoustic stimulators [Patent No. U.S. Pat. No. 5,903,516, entitled Acoustic force generator for detection, imaging and information transmission using the beat signal of multiple intersecting sonic beams, to GREENLEAF et al].

Third, the scalar potential $\phi$ in the above equation $\partial \phi / \partial n = \sigma(r)$ may be manipulated to shape the electric field. For example, this is accomplished by changing the boundaries of conductor/air (or non-conductor) interfaces, thereby creating different boundary conditions. For example, the conducting material may pass through conducting apertures in an insulated mesh before contacting the patient's skin, creating thereby an array of electric field maxima. As another example, an electrode may be disposed at the end of a long tube that is filled with conducting material, or the electrode may be situated at the bottom of a curved cup that is filled with conducting material. In those cases the dimensions of the tube or cup would affect the resulting electric fields and currents.

Fourth, the conductivity $\sigma$ (in the equation $J = \sigma E$) may be varied spatially within the device by using two or more different conducting materials that are in contact with one another, for given boundary conditions. The conductivity may also be varied by constructing some conducting material from a semiconductor, which allows for adjustment of the conductivity in space and in time by exposure of the semiconductor to agents to which they are sensitive, such as electric fields, light at particular wavelengths, temperature, or some other environmental variable over which the user of the device has control. For the special case in which the semiconductor's conductivity may be made to approach zero, that would approximate the imposition of an interfacial boundary condition as described in the previous paragraph.

Fifth, a dielectric material having a high permittivity $\epsilon$, such as Mylar, neoprene, titanium dioxide, or strontium titanate, may be used in the device, for example, in order to permit capacitative electrical coupling to the patient's skin. Changing the permittivity in conjunction along with changing the waveform V(t) would especially affect operation of the device, because the permittivity appears in a term that is a function of the time-derivative of the electric potential: $\nabla \cdot (\epsilon \nabla (\partial \phi / \partial t))$.

In configurations of the present invention, an electrode is situated in a container that is filled with conducting material. In one embodiment, the container contains holes so that the conducting material (e.g., a conducting gel) can make physical contact with the patient's skin through the holes. For example, the conducting medium 350 in FIG. 1 may comprise a chamber surrounding the electrode, filled with a conductive gel that has the approximate viscosity and mechanical consistency of gel deodorant (e.g., Right Guard Clear Gel from Dial Corporation, 15501 N. Dial Boulevard, Scottsdale Ariz. 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is less viscous than conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the invention, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue.

Agar can also be used as part of the conducting medium, but it is not preferred, because agar degrades in time, is not ideal to use against skin, and presents difficulties with cleaning the patient. Rather than using agar as the conducting medium, an electrode can instead be in contact with in a conducting solution such as 1-10% NaCl that also contacts an electrically conducting interface to the human tissue. Such an interface is useful as it allows current to flow from the electrode into the tissue and supports the conducting medium, wherein the device can be completely sealed. Thus, the interface is material, interposed between the conducting medium and patient's skin, that allows the conducting medium (e.g., saline solution) to slowly leak through it, allowing current to flow to the skin. Several interfaces are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J Martens. Conducting polymer-hydrogels for medical electrode applications. Sci. Technol. Adv. Mater. 11 (2010) 014107 (13 pp)]. For example it may be the following hypoallergenic, bacteriostatic electrode gel: SIGNAGEL Electrode Gel from Parker Laboratories, Inc., 286 Eldridge Rd., Fairfield N.J. 07004. Another example is the KM10T hydrogel from Katecho Inc., 4020 Gannett Ave., Des Moines Iowa 50321.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the electrode and conducting solution in from the tissue, yet allow current to pass.

The stimulator 340 in FIG. 1 shows two equivalent electrodes, side-by-side, wherein electrical current would pass through the two electrodes in opposite directions. Thus, the current will flow from one electrode, through the tissue and back through the other electrode, completing the circuit within the electrodes' conducting media that are separated from one another. An advantage of using two equivalent electrodes in this configuration is that this design will increase the magnitude of the electric field gradient between them, which is important for exciting long, straight axons such as the vagus nerve in the neck and other deep peripheral nerves.

Figure 3A:
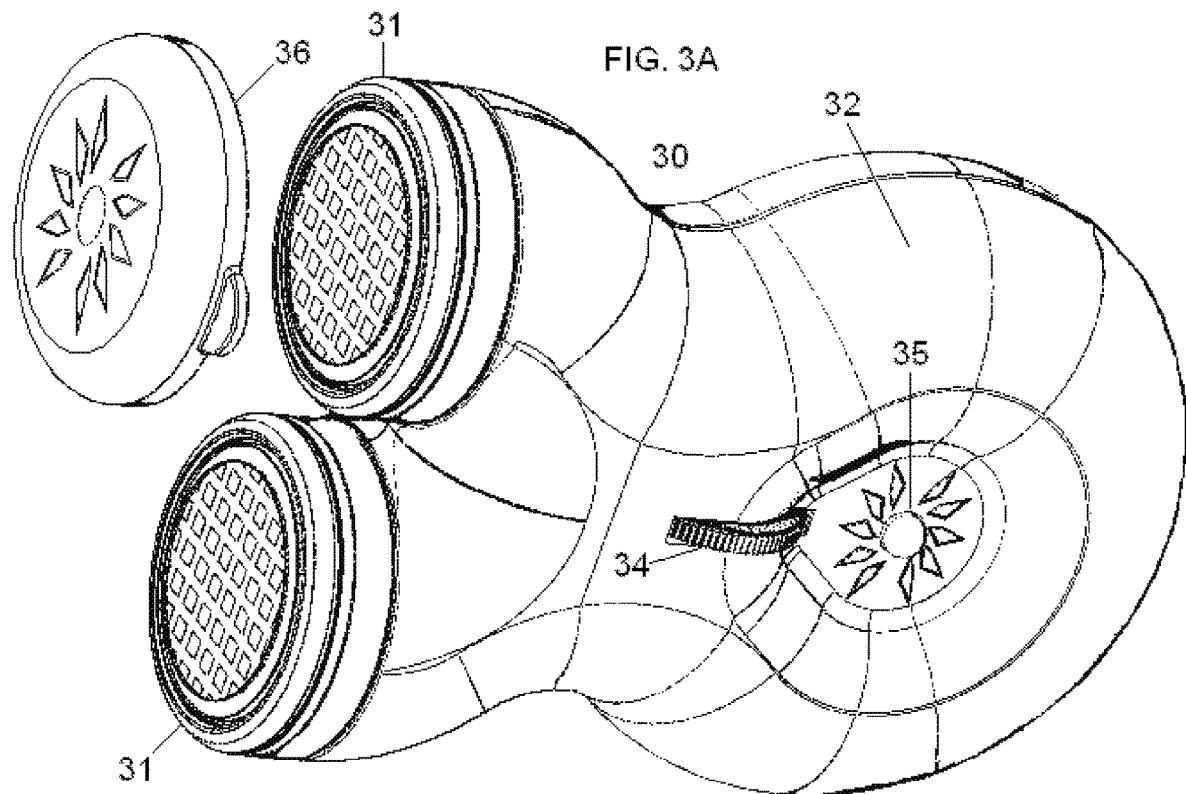
FIG. 3A is a perspective view of a dual-electrode stimulator according to an embodiment of the present invention.
Figure 3B:
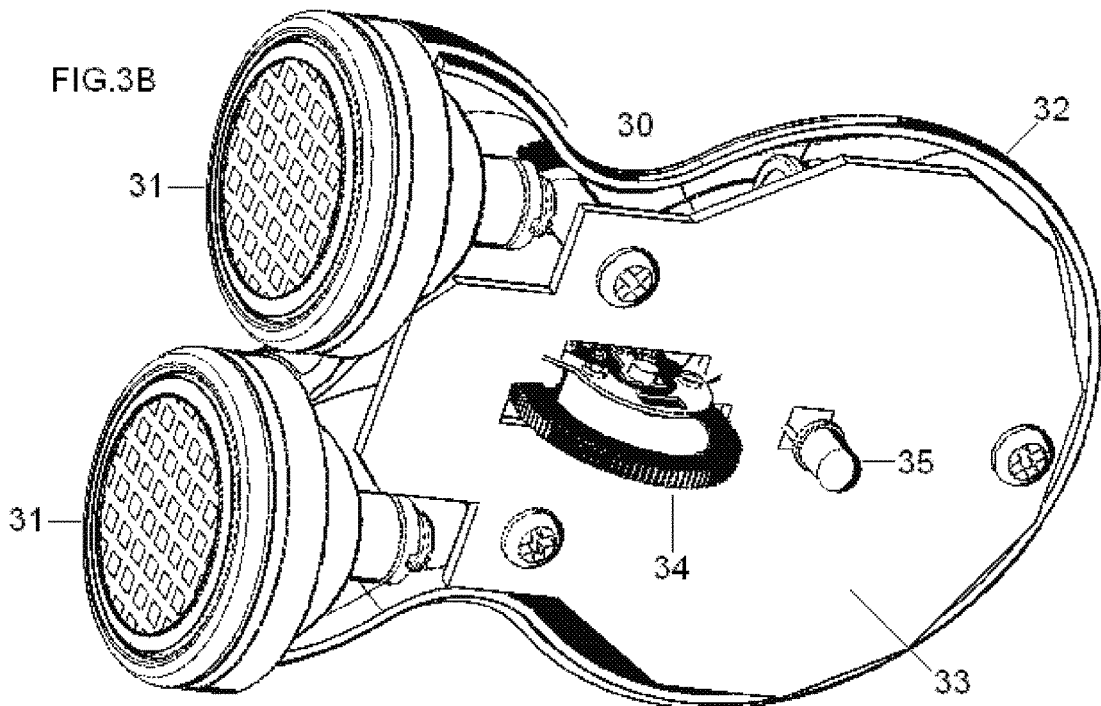
FIG. 3B is a cut-a-way view of the dual-electrode stimulator of FIG. 3A, illustrating the stimulator's electrodes and electronic components.

A preferred embodiment of the stimulator is shown in FIG. 3A. A cross-sectional view of the stimulator along its long axis is shown in FIG. 3B. As shown, the stimulator (30) comprises two heads (31) and a body (32) that joins them. Each head (31) contains a stimulating electrode. The body of the stimulator (32) contains the electronic components and battery (not shown) that are used to generate the signals that drive the electrodes, which are located behind the insulating board (33) that is shown in FIG. 3B. However, in other embodiments of the invention, the electronic components that generate the signals that are applied to the electrodes may be separate, but connected to the electrode head (31) using wires. Furthermore, other embodiments of the invention may contain a single such head or more than two heads.

Heads of the stimulator (31) are applied to a surface of the patient's body, during which time the stimulator may be held in place by straps or frames (not shown), or the stimulator may be held against the patient's body by hand. In either case, the level of stimulation power may be adjusted with a wheel (34) that also serves as an on/off switch. A light (35) is illuminated when power is being supplied to the stimulator. A cap (36) is provided to cover each of the stimulator heads (31), to protect the device when not in use, to avoid accidental stimulation, and to prevent material within the head from leaking or drying. Thus, in this embodiment of the invention, mechanical and electronic components of the stimulator (impulse generator, control unit, and power source) are compact, portable, and simple to operate. A cap

(36) is provided to cover each of the stimulator heads (31), to protect the device when not in use, to avoid accidental stimulation, and to prevent material within the head from leaking or drying. However, for embodiments of the stimulator head in which the head is covered with Mykir or some other high-dielectric material that can capacitively couple the signal to the skin, the Mylar may completely seal the gel within the stimulator head, thereby preventing exposure of the gel to the outside. In that case, there would be no gel evaporation. Then, the cap (36) would be less advantageous because the head can be cleaned between stimulation sessions (e.g., with isopropyl alcohol) with no chance of contaminating the internal gel.

Construction of the stimulator head is shown in more detail in FIG. 4. In the embodiment shown in FIGS. 4A and 4B, the stimulator head contains an aperture screen, but in the embodiment shown in FIGS. 4C and 4D, there is no aperture screen. Referring now to the exploded view shown in FIG. 4A, the electrode head is assembled from a snap-on cap (41) that serves as a tambour for a conducting membrane (42), an aperture screen (43), the head-cup (44), the electrode which is also a screw (45), and a lead-mounting screw (46) that is inserted into the electrode (45). The electrode (45) seen in each stimulator head has the shape of a screw that is flattened on its tip. Pointing of the tip would make the electrode more of a point source, such that the above-mentioned equations for the electrical potential may have a solution corresponding more closely to a far-field approximation. Rounding of the electrode surface or making the surface with another shape will likewise affect the boundary conditions. Completed assembly of the stimulator head is shown in FIG. 4B, which also shows how the head is attached to the body of the stimulator (47).

As examples, the conducting membrane (42) may be a sheet of Tecophlic material from Lubrizol Corporation, 29400 Lakeland Boulevard, Wickliffe, Ohio 44092. The apertures may be open, or they may be plugged with conducting material, for example, KM10T hydrogel from Katecho Inc., 4020 Gannett Ave., Des Moines Iowa 50321. If the apertures are so-plugged, the conducting membrane (42) becomes optional. The head-cup (44) is filled with conducting material, for example, SIGNAGEL Electrode Gel from Parker Laboratories, Inc., 286 Eldridge Rd., Fairfield N.J. 07004. The snap-on cap (41), aperture screen (43), head-cup (44) and body of the stimulator are made of a non-conducting material, such as acrylonitrile butadiene styrene. The depth of the head-cup from its top surface to the electrode may be between one and six centimeters. The head-cup may have a different curvature than what is shown in FIG. 4, or it may be tubular or conical or have some other inner surface geometry that will affect the Neumann boundary conditions.

The stimulator is preferably configured such that the distribution of current passing into the patient's tissue is substantially uniform to minimize high current densities that would potentially cause pain to the patient. In one exemplary embodiment, the electrode(s) are preferably spaced from the conducting membrane 42 by a distance of about 0.25 to 4 times the diameter of the conducting membrane 42. Thus, if the diameter of the conducting membrane 42 is 1 inch then the electrode should be between 0.25 and 4 inches from the conducting membrane, preferably about 0.5 to 2 inches. In addition, in order to reach a nerve at a depth d, the electrode diameter should be between 0.2 and 2 d, preferable about 1 d and the spacing (from center to center) should be between 1.5 d and 3 d, preferable about 2 d. The conducting medium preferably has a conductivity that is high enough to allow current flow therethrough, but low enough to minimize a non-uniform distribution of current passing through the conducting membrane 42 into the patient's tissue.

The alternate embodiment of the stimulator head that is shown in FIG. 4C also contains a snap-on cap (41), a conducting membrane (42), the head-cup (44), the electrode which is also a screw (45), and a lead-mounting screw (46) that is inserted into the electrode (45). This alternate embodiment differs from the embodiment shown in FIGS. 4A and 4B in regard to the mechanical support that is provided to the conducting membrane (42). Whereas the aperture screen had provided mechanical support to the membrane in the other embodiment, in the alternate embodiment a reinforcing ring (40) is provided to the membrane. That reinforcement ring rests on non-conducting struts (49) that are placed in the head-cup (44), and a non-conducting strut-ring (48) is placed within notches in the struts (49) to hold the struts in place. An advantage of the alternate embodiment is that without apertures, current flow is less restricted through the conducting membrane (42). Furthermore, although the struts and strut-ring are made of non-conducting material in this alternate embodiment, the design may be adapted to position additional electrode or other conducting elements within the head-cup for other more specialized configurations of the stimulator head, the inclusion of which will influence the electric fields that are generated by the device. Completed assembly of the alternate stimulator head is shown in FIG. 4D, without showing attachment to the body of the stimulator, and without showing the insertion of the lead-mounting screw (46). In fact, it is also possible to insert a lead under the head of the electrode (45), and many other methods of attaching the electrode to the signal-generating electronics of the stimulator are known in the art.

Another embodiment of the stimulator is shown in FIG. 5, showing a device in which electrically conducting material is dispensed from the device to the patient's skin. FIGS. 5A and 5B respectively provide top and bottom views of the outer surface of the electrical stimulator 50. FIG. 5C provides a bottom view of the stimulator 50, after sectioning along its long axis to reveal the inside of the stimulator.

FIGS. 5A and 5C show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 5A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

FIGS. 5B and 5C show the bottom of the self-contained stimulator 50. An on/off switch 52 is attached through a port 54, and a power-level controller 53 is attached through another port 54. The switch is connected to a battery power source (320 in FIG. 1), and the power-level controller is attached to the control unit (330 in FIG. 1) of the device. The power source battery and power-level controller, as well as the impulse generator (310 in FIG. 1) are located (but not shown) in the rear compartment 55 of the housing of the stimulator 50.

Individual wires (not shown) connect the impulse generator (310 in FIG. 1) to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel (350 in FIG. 1) to each head compartment 57. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another.

In the preferred embodiments, electrodes are made of a metal, such as stainless steel. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18(2, 2008):35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004): 346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20 (1, 1994):29-35].

For example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes. Annu. Rev. Biomed. Eng. 2008. 10:275-309; Michael F. NOLAN. Conductive differences in electrodes used with transcutaneous electrical nerve stimulation devices. Physical Therapy 71 (1991):746-751].

Although the electrode may consist of arrays of conducting material, the embodiments shown in FIGS. 3 to 5 avoid the complexity and expense of array or grid electrodes [Ana POPOVIC-BIJELIC, Goran Bijelic, Nikola Jorgovanovic, Dubravka Bojanic, Mirjana B. Popovic, and Dejan B. Popovic. Multi-Field Surface Electrode for Selective Electrical Stimulation. Artificial Organs 29 (6, 2005):448-452; Dejan B. POPOVIC and Mirjana B. Popovic. Automatic determination of the optimal shape of a surface electrode: Selective stimulation. Journal of Neuroscience Methods 178 (2009) 174-181; Thierry KELLER, Marc Lawrence, Andreas Kuhn, and Manfred Morari. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197]. This is because the designs shown in FIGS. 3 to 5 provide a uniform surface current density, which would otherwise be a potential advantage of electrode arrays, and which is a trait that is not shared by most electrode designs [Kenneth R. BRENNEN. The Characterization of Transcutaneous Stimulating Electrodes. IEEE Transactions on Biomedical Engineering BME-23 (4, 1976): 337-340; Andrei PATRICIU, Ken Yoshida, Johannes J. Struijk, Tim P. DeMonte, Michael L. G. Joy, and Hans Stødkilde-Jørgensen. Current Density Imaging and Electrically Induced Skin Burns Under Surface Electrodes. IEEE Transactions on Biomedical Engineering 52 (12, 2005): 2024-2031; R. H. GEUZE. Two methods for homogeneous field defibrillation and stimulation. Med. and Biol. Eng. and Comput. 21(1983), 518-520; J. PETROFSKY, E. Schwab, M. Cuneo, J. George, J. Kim, A. Almalty, D. Lawson, E. Johnson and W. Remigo. Current distribution under electrodes in relation to stimulation current and skin blood flow: are modern electrodes really providing the current distribution during stimulation we believe they are? Journal of Medical Engineering and Technology 30 (6, 2006): 368-381; Russell G. MAUS, Erin M. McDonald, and R. Mark Wightman. Imaging of Nonuniform Current Density at Microelectrodes by Electrogenerated Chemiluminescence. Anal. Chem. 71 (1999): 4944-4950]. In fact, patients found the design shown in FIGS. 3 to 5 to be less painful in a direct comparison with a commercially available grid-pattern electrode [UltraStim grid-pattern electrode, Axelggard Manufacturing Company, 520 Industrial Way, Fallbrook Calif., 2011].

The stimulator designs shown in FIGS. 3 to 5 situate the electrode remotely from the surface of the skin within a chamber, with conducting material placed in the chamber between the skin and electrode. Such a chamber design had been used prior to the availability of flexible, flat, disposable electrodes [Patent U.S. Pat. No. 3,659,614, entitled Adjustable headband carrying electrodes for electrically stimulating the facial and mandibular nerves, to Jankelson; U.S. Pat. No. 3,590,810, entitled Biomedical body electrode, to Kopecky; U.S. Pat. No. 3,279,468, entitled Electrotherapeutic facial mask apparatus, to Le Vine; U.S. Pat. No. 6,757,556, entitled Electrode sensor, to Gopinathan et al; U.S. Pat. No. 4,383,529, entitled Iontophoretic electrode device, method and gel insert, to Webster; U.S. Pat. No. 4,220,159, entitled Electrode, to Francis et al. U.S. Pat. Nos. 3,862,633, 4,182,346, and 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing bioelectrode, to Jacobsen et al.] The stimulator designs shown in FIGS. 3 to 5 are also self-contained units, housing the electrodes, signal electronics, and power supply. Portable stimulators are also known in the art, for example, patent U.S. Pat. No. 7,171,266, entitled Electro-acupuncture device with stimulation electrode assembly, to Gruzdowich]. One of the novelties or the present invention is that two or more remote electrodes are configured for placement relative to the axis of a deep, long nerve, such that the stimulator along with a correspondingly suitable stimulation waveform shapes the electric field, producing a selective physiological response by stimulating that nerve, but avoiding substantial stimulation of nerves and tissue other than the target nerve, particularly avoiding the stimulation of nerves that produce pain.

Examples in the remaining disclosure will be directed to methods for using the disclosed electrical stimulation devices for treating a patient. These applications involve stimulating the patient in and around the patient's neck. However, it will be appreciated that the systems and methods of the present invention might be applied equally well to other nerves of the body, including but not limited to parasympathetic nerves, sympathetic nerves, and spinal or cranial nerves. As examples, the disclosed devices may used to treat particular medical conditions, by substituting the devices disclosed herein for the stimulators disclosed in the following patent applications.

Applicant's commonly assigned patent application, Ser. No. 12/964,050, entitled Magnetic Stimulation Devices and Methods of Therapy, disclosed methods for using the device to treat such conditions as post-operative ileus, dysfunction associated with TNF-alpha in Alzheimer's disease, postoperative cognitive dysfunction, rheumatoid arthritis, bronchoconstriction, urinary incontinence and/or overactive bladder, and sphincter of Oddi dysfunction.

Another commonly assigned application, Ser. No. 13/005,005, entitled Non-invasive Treatment of Neurodegenerative Diseases, disclosed methods and devices for treating neurodegenerative diseases more generally, including essential tremor, Alzheimer's disease and its precursor mild cognitive impairment (MCI), Parkinson's disease (including Parkinson's disease dementia) and multiple sclerosis, as well as postoperative cognitive dysfunction and postoperative delirium. The devices and methods may also be used to treat conditions that were not disclosed in those patent applications, such as allergic rhinitis, headaches, particularly tension headaches, cluster headaches, sinus headaches and migraine headaches [Alberto Proietti CECCHINI, Eliana Mea, Vincenzo Tullo, Marcella Curone, Angelo Franzini, Giovanni Broggi, Mario Savino, Gennaro Bussone, Massimo Leone. Vagus nerve stimulation in drug-resistant daily chronic migraine with depression: preliminary data. Neurol Sci (2009) 30 (Suppl 1):S101-S104].

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retropharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6:
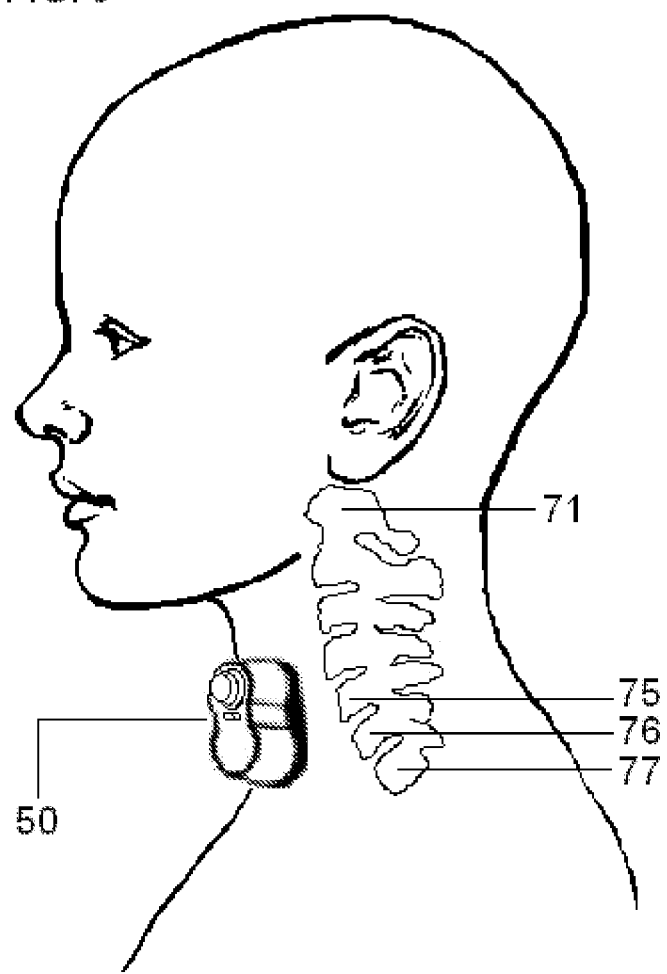
FIG. 6 illustrates an approximate position of a housing of the dual-electrode stimulator according one embodiment of the present invention, when the electrodes used to stimulate the vagus nerve in the neck of a patient.

FIG. 6 illustrates use of the devices shown in FIGS. 3 to 5 to stimulate the vagus nerve at that location in the neck, in which the stimulator device 50 in FIG. 5 is shown to be applied to the target location on the patient's neck as described above. For reference, locations of the following vertebrae are also shown: first cervical vertebra 71, the fifth cervical vertebra 75, the sixth cervical vertebra 76, and the seventh cervical vertebra 77.

Figure 7:
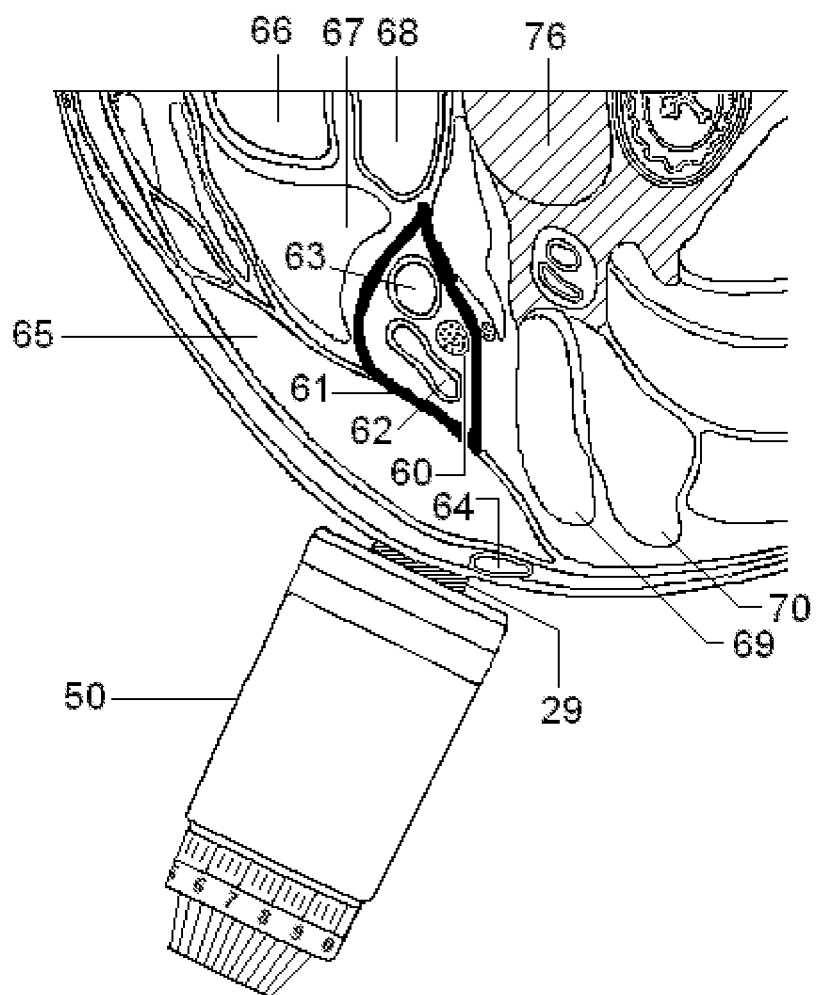
FIG. 7 illustrates the housing of the dual-electrode stimulator according one embodiment of the present invention, as the electrodes are positioned to stimulate the vagus nerve in a patient's neck via electrically conducting gel (or some other conducting material), which is applied to the surface of the neck in the vicinity of the identified anatomical structures.

FIG. 7 provides a more detailed view of use of the electrical stimulator, when positioned to stimulate the vagus nerve at the neck location that is indicated in FIG. 6. As shown, the stimulator 50 in FIG. 5 touches the neck indirectly, by making electrical contact through conducting gel 29 (or other conducting material) which may be is dispensed through mesh openings (identified as 51 in FIG. 5) of the stimulator or applied as an electrode gel or paste. The layer of conducting gel 29 in FIG. 7 is shown to connect the device to the patient's skin, but it is understood that the actual location of the gel layer(s) may be generally determined by the location of mesh 51 shown in FIG. 5. Furthermore, it is understood that for other embodiments of the invention, the conductive head of the device may not necessitate the use of additional conductive material being applied to the skin. The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

If it is desired to maintain a constant intensity of stimulation in the vicinity of the vagus nerve (or any other nerve or tissue that is being stimulated), methods may also be employed to modulate the power of the stimulator in order to compensate for patient motion or other mechanisms that would otherwise give rise to variability in the intensity of stimulation. In the case of stimulation of the vagus nerve, such variability may be attributable to the patient's breathing, which may involve contraction and associated change in geometry of the sternocleidomastoid muscle that is situated close to the vagus nerve (identified as 65 in FIG. 7). Methods for compensating for motion and other confounding factors were disclosed by the present applicant in commonly assigned application Ser. No. 12/859,568, entitled Non-Invasive Treatment of Bronchial Constriction, to SIMON, which is hereby incorporated by reference.

Methods of treating a patient comprise stimulating the vagus nerve as indicated in FIGS. 6 and 7, using the electrical stimulation devices that are disclosed herein. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to produce a therapeutic result in the patient. Stimulation parameters for each patient are adjusted on an individualized basis. Ordinarily, the amplitude of the stimulation signal is set to the maximum that is comfortable for the patient, and then the other stimulation parameters are adjusted.

In other embodiments of the invention, pairing of vagus nerve stimulation may be with a time-varying sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect. For example, the hypothalamus is well known to be responsive to the presence of bright light, so exposing the patient to bright light that is fluctuating with the same stimulation frequency as the vagus nerve (or a multiple of that frequency) may be performed in an attempt to enhance the role of the hypothalamus in producing the desired therapeutic effect. Such paired stimulation does not rely upon neuronal plasticity and is in that sense different from other reports of paired stimulation [Navzer D. ENGINEER, Jonathan R. Riley, Jonathan D. Seale, Will A. Vrana, Jai A. Shetake, Sindhu P. Sudanagunta, Michael S. Borland and Michael P. Kilgard. Reversing pathological neural activity using targeted plasticity. Nature (2011): published online doi:10.1038/nature09656].

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method comprising:
   generating an electrical signal within a housing having a lead extending therefrom, wherein the electrical signal generated within the housing comprises bursts of pulses, wherein each burst of pulses comprises a burst period and a constant period, wherein the signal includes 2 pulses to 20 pulses within each burst period, wherein the signal includes zero pulses within each constant period, wherein each burst period and constant period together have a combined frequency from about 15 Hz to about 50 Hz, and, wherein the pulses alternate between a positive voltage and a negative voltage within each of the burst periods;
   positioning the lead near, or in operational proximity to, a spinal nerve within a patient; and
   emitting the electrical signal via the lead towards the spinal nerve such that the patient experiences at least some pain relief.

2. The method of claim 1, wherein the pulses comprise a full sinusoidal wave.

3. The method of claim 1, wherein the pulses are not emitted during the constant periods.

4. The method of claim 3 further comprising suspending the pulses during the constant periods.

5. The method of claim 1, wherein the lead includes an electrode, and further comprising positioning the electrode near, or in operational proximity to, the spinal nerve and applying a voltage to the electrode such that an electric field is created at or near the spinal nerve.

6. The method of claim 5 further comprising varying the voltage such that a charge of the electric field emitted during each of the burst period alternates between positive and negative.

7. The method of claim 5, wherein the electric field emitted during the constant periods has a magnitude of zero.

8. The method of claim 1 wherein each of the pulses has a duration of about 50 microseconds to about 1,000 microseconds.

9. The method of claim 1, wherein at least one of the pulses has a duration of about 100 to about 400 microseconds.

10. The method of claim 1, wherein the burst periods each comprise 4 pulses to 10 pulses.

11. The method of claim 1, wherein emitting an electrical signal comprises positioning an electrode in operational proximity to the spinal nerve, and delivering a sufficient amount of the electrical signal such that the patient experiences at least some pain relief.

12. The method of claim 1, wherein the burst periods each have a duration of less than about 20,000 microseconds.

13. The method of claim 1, wherein the burst periods each have a duration of less than about 2,000 microseconds.

14. The method of claim 1, wherein the burst periods each have a duration of about 1,000 microseconds.

15. A device comprising:
    a housing;
    a lead extending from the housing, wherein the lead is configured to be positioned near, or in operational proximity to, a spinal nerve;
    a source of energy positioned within the housing, wherein the source of energy is operably coupled to the lead; and
    a signal generator configured for generating an electrical signal comprising burst of pulses, wherein each burst of pulses comprises a burst period and a constant period, wherein the signal includes 2 pulses to 20 pulses within each burst period, wherein the signal includes zero pulses within each constant period, wherein each burst period and constant period together have a combined frequency from about 15 Hz to about 50 Hz and wherein the source of energy alternates the pulses between a positive voltage and a negative voltage within each of the burst periods; and
    wherein the source of energy is configured to emit the electrical signal via the lead towards a target area of the spinal nerve such that a patient experiences at least some pain relief.

16. The device of claim 15, wherein the pulses are not emitted during the constant periods.

17. The device of claim 15, wherein the lead includes an electrode, wherein the source of energy applies a voltage to the electrodes such that an electric field is created at or near the spinal nerve.

18. The device of claim 17, wherein the source of energy varies the voltage such that a charge of the electric field emitted during each of the burst periods alternates between positive and negative.

19. The device of claim 18, wherein the electric field emitted during each constant period has a magnitude of zero.

20. The device of claim 18, wherein each of the pulses has a duration of about 50 microseconds to about 1,000 microseconds.

21. The device of claim 15, wherein the lead includes an electrode, wherein the electrode is configured to be positioned in operational proximity to the spinal nerve, and the source of energy delivers a sufficient amount of the electrical signal such that the patient experiences at least some pain relief.

* * * * *